US012624372B2

(12) United States Patent
Bensoussan et al.

(10) Patent No.: US 12,624,372 B2
(45) Date of Patent: May 12, 2026

(54) MEANS AND METHODS FOR PRODUCING ISOBUTENE FROM 3-METHYLCROTONIC ACID

(71) Applicant: Global Bioenergies, Evry Cedex (FR)

(72) Inventors: Claude Bensoussan, Paris (FR); Frederic Ollivier, Villeurbanne (FR); Romain Chayot, Paris (FR); Denis Thibaut, Paris (FR); Marc Delcourt, Paris (FR)

(73) Assignee: Global Bioenergies, Evry Cedex (FR)

( * ) Notice: Subject to any disclaimer, the term of this patent is extended or adjusted under 35 U.S.C. 154(b) by 371 days.

(21) Appl. No.: 18/258,544

(22) PCT Filed: Dec. 20, 2021

(86) PCT No.: PCT/EP2021/086687
§ 371 (c)(1),
(2) Date: Jun. 20, 2023

(87) PCT Pub. No.: WO2022/136207
PCT Pub. Date: Jun. 30, 2022

(65) Prior Publication Data
US 2025/0270595 A1     Aug. 28, 2025

(30) Foreign Application Priority Data
Dec. 21, 2020     (EP) ..................................... 20215872

(51) Int. Cl.
| | | |
|---|---|---|
| *C12P 7/40* | (2006.01) | |
| *C12N 9/10* | (2006.01) | |
| *C12N 9/88* | (2006.01) | |
| *C12P 5/02* | (2006.01) | |

(52) U.S. Cl.
CPC ............ *C12P 5/026* (2013.01); *C12N 9/1085* (2013.01); *C12N 9/88* (2013.01); *C12Y 401/01063* (2013.01)

(58) Field of Classification Search
CPC ............. C12P 5/026; C12Y 103/01086; C12N 9/93; C12N 15/52
See application file for complete search history.

(56) References Cited

U.S. PATENT DOCUMENTS

2018/0371503 A1*  12/2018  Allard ............ C12Y 207/02015

FOREIGN PATENT DOCUMENTS

| | | |
|---|---|---|
| WO | 2016042012 A1 | 3/2016 |
| WO | 2017085167 A2 | 5/2017 |
| WO | 2018206262 A1 | 11/2018 |
| WO | 2020188033 A1 | 9/2020 |

OTHER PUBLICATIONS

International Search Report and the Written Opinion of the International Searching Authority Received in the Corresponding PCT Application.

* cited by examiner

*Primary Examiner* — Tekchand Saidha
(74) *Attorney, Agent, or Firm* — Michele Wales; InHouse Patent Counsel

(57)     ABSTRACT
Described is a method for the production of isobutene from a carbon source characterized in that it comprises: (a) culturing a microorganism capable of producing 3-methylcrotonic acid from a carbon source in a liquid culture medium, thereby producing 3-methylcrotonic acid so that it accumulates in the liquid culture medium; and (b) enzymatically converting 3-methylcrotonic acid contained in the liquid culture medium obtained in step (a) into isobutene by: (i) incubating a microorganism expressing ap FMN-dependent decarboxylase associated with an FMN prenyl transferase with liquid culture medium containing 3-methylcrotonic acid obtained in step (a); and/or (ii) incubating a FMN-dependent decarboxylase associated with a FMN prenyl transferase with liquid culture medium containing 3-methylcrotonic acid obtained in step (a); thereby producing isobutene; and (c) recovering the produced isobutene.

18 Claims, 9 Drawing Sheets

Figure 1:
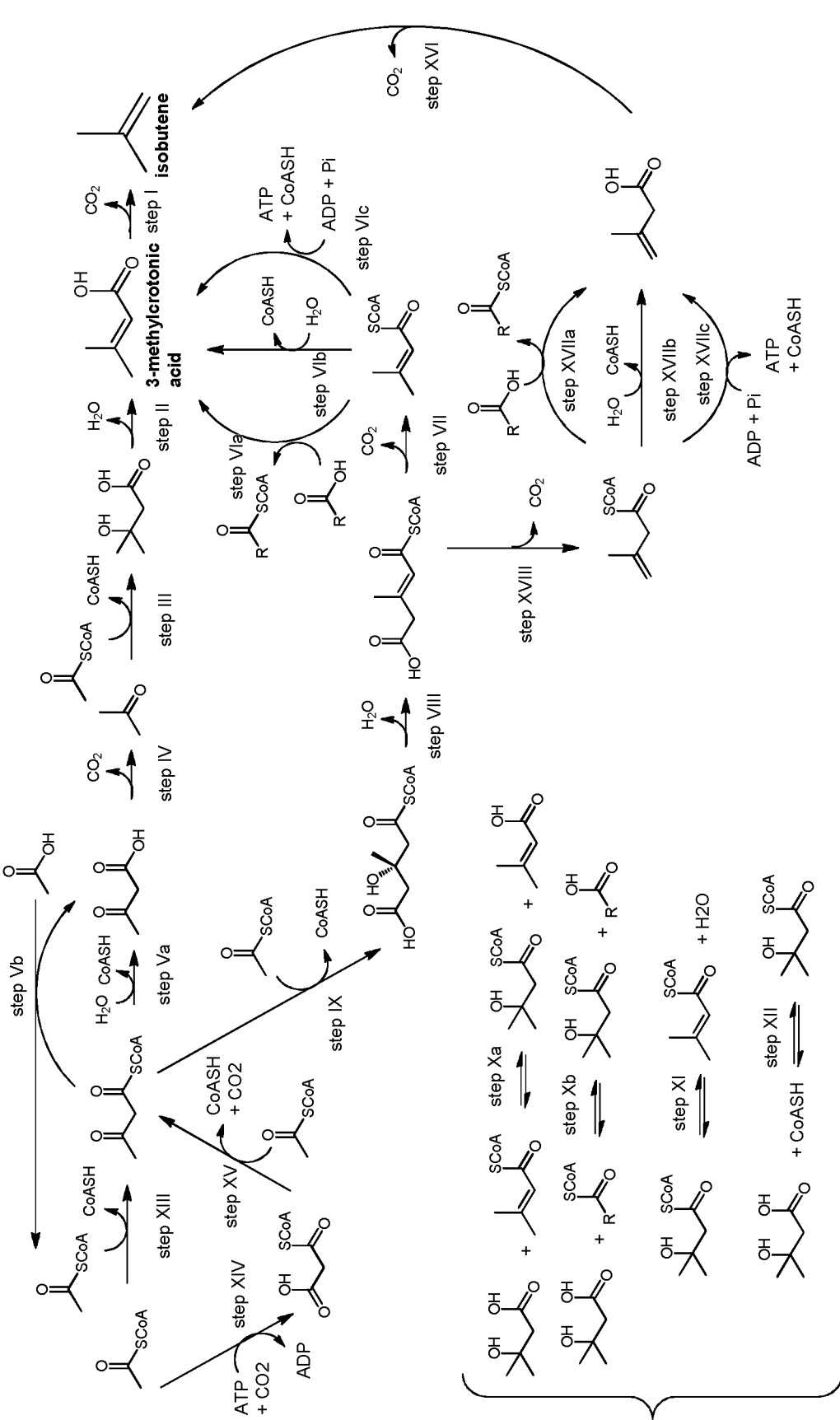

Specification includes a Sequence Listing.

1 vvm 0.05 vvm 0 vvm

——— 1 vvm

——— 0.05 vvm

——— 0 vvm

SEQUENCE LISTING

<160> NUMBER OF SEQ ID NOS: 1

<210> SEQ ID NO 1
<211> LENGTH: 10770
<212> TYPE: DNA
<213> ORGANISM: Artificial Sequence
<220> FEATURE:
<223> OTHER INFORMATION: recombinant pGB 5550 plasmid

<400> SEQUENCE: 1

```
ctcactactt tagtcagttc cgcagtatta caaaaggatg tcgcaaacgc tgtttgctcc        60
tctacaaaac agaccttaaa accctaaagg cttaagtagc accctcgcaa gctcgggcaa       120
atcgctgaat attccttttg tctccgacca tcaggcacct gagtcgctgt ctttttcgtg       180
acattcagtt cgctgcgctc acggctctgg cagtgaatgg gggtaaatgg cactacaggc       240 gcctttatg gattcatgca aggaaactac ccataataca agaaaagccc gtcacgcttc        300
tcagggcgtt ttatggcggg tctgctatgt ggtgctatct gactttttgc tgttcagcag       360
ttcctgccct ctgattttcc agtctgaccc tagtcaaggc cttaagtgag tcgtattacg       420
gactggccgt cgttttacaa cgtcgtgact gggaaaaccc tggcgttacc caacttaatc       480
gccttgcagc acatccccct ttcgccagct ggcgtaatag cgaagaggcc cgcaccgatc       540
gcccttccca acagttgcgc agcctgaatg gcgaatggcg cctgatgcgg tattttctcc       600
ttacgcatct gtgcggtatt tcacaccgcc cggggaacta tagtttaaac ttttcaatga       660
attcatttaa gcggccgcat caattctaga atttaaatag tcaaaagcct ccgaccggag       720
gcttttgact gaccctattga caattaaagg ctaaaatgct ataattccac taatagaaat       780
aattttgttt aactttaggt ctctatcgta agaaggagat acatatga aagaagtggt          840 gattgccagc gcagttcgta ccgcaattgg tagctatggt aaaagcctga aagatgttcc       900
ggcagttgat ctgggtgcaa ccgcaattaa agaagcagtt aaaaaagccg gtattaaacc       960
ggaagatgtg aacgaagtta ttctgggtaa tgttctgcaa gcaggtctgg gtcagaatcc      1020
ggcacgtcag gcctcgttta aagcaggtct gccggttgaa attccggcaa tgaccattaa      1080
caaagtttgt ggtagcggtc tgcgtaccgt tagcctggca gcacagatta tcaaagccgg      1140
tgatgcagat gttattattg ccggtggtat ggaaaatatg agccgtgcac cgtatctggc      1200
aaataatgca cgttgggggtt atcgtatggg taatgccaaa tttgtggatg agatgattac      1260
cgatggtctg tgggatgcct ttaatgatta tcacatgggt attaccgcag agaatattgc      1320
agaacgttgg aatattagcc gtgaagaaca ggatgaattt gcactggcaa gccagaaaaa      1380
agcagaagaa gcaattaaaa gcggtcagtt caaagatgaa attgtgccgg ttgttatcaa      1440
aggtcgtaaa ggtgaaaccg ttgttgatac cgatgaacat ccgcgtttTg gtagcaccat      1500
tgaaggtctg gcaaaactga aaccggcatt caaaaaagat ggcaccgtta ccgcaggtaa      1560
tgcaagcggt ctgaatgatt gtgcagcagt tctggttatt atgagcgcag aaaaagcaaa      1620
agaactgggt gttaaaccgc tggcaaaaat tgtgagctat ggtagtgccg gtgttgatcc      1680
ggcaattatg ggttatggtc cgtttttatgc aaccaaagca gcaattgaaa aagcaggttg      1740
gaccgttgat gaactggatc tgattgaaag caatgaagca tttgcagcac agagcctggc      1800
```

-continued

```
agttgcaaaa gacctgaaat tcgatatgaa taaagtgaat gtgaatggcg gtgcaattgc      1860
cctgggtcat ccgattggtg caagcggtgc acgtattctg gttaccctgg ttcatgcaat      1920
gcagaaacgt gatgcaaaaa aaggtctggc caccctgtgt attggtggtg gtcagggcac      1980
cgcaattctg ctggaaaaat gctaataagc ttgaaggaga tataatgacc attggtattg      2040
ataaaatcag ctttttcgtg cctccgtact atattgatat gaccgcactg gccgaagcac      2100
gtaatgttga tccgggtaaa tttcatattg gtattggtca ggatcagatg gccgttaatc      2160
cgattagcca ggatattgtt acctttgcag caaatgcagc agaagcaatt ctgaccaaag      2220
aagataaaga ggccattgat atggttattg ttggcaccga aagcagcatt gatgaaagca      2280
aagcagcagc agttgttctg catcgtctga tgggtattca gccgtttgca cgtagctttg      2340
aaattaaaga agcatgttac ggagcaaccg caggtctgca actggcaaaa aatcatgttg      2400
cactgcatcc ggataaaaaa gttctggttg ttgcagcaga tattgccaaa tatggtctga      2460
atagcggtgg tgaaccgacc cagggtgccg gtgcagttgc aatgctggtt gcaagcgaac      2520
cgcgtattct ggcactgaaa gaagataatg ttatgctgac ccaggatatt tatgattttt      2580
ggcgtccgac cggtcatccg tatccgatgg ttgatggtcc gctgagcaat gaaacctata      2640
ttcagagctt tgcacaggtg tgggatgaac ataaaaaacg taccggtctg gatttcgcag      2700
attatgatgc actggcattt catatcccgt ataccaaaat gggtaaaaaa gcactgctgg      2760
ccaaaattag cgatcagacc gaagccgaac aagaacgcat tctggcacgt tatgaagaaa      2820
gcattgttta tagccgtcgt gtgggtaatc tgtataccgg tagcctgtat ctgggtctga      2880
ttagcctgct ggaaaatgca accaccctga ccgcaggtaa tcagattggt ctgtttagct      2940
atggtagcgg tgccgttgca gaattttttca caggtgaact ggttgcaggt tatcagaatc      3000
atctgcaaaa agaaacccat ctggcactgc tggataatcg taccgaactg agcattgcag      3060
aatatgaagc aatgtttgca gaaaccctgg ataccgatat tgatcagacc ctggaagatg      3120
aactgaaata tagcattagc gccattaata caccgtgcg tagctatcgt aactaataag      3180
gtagaaggag atataatgcc ggaatttaaa gttgatgcac gtggtccgat tgaaatctgg      3240
accattgatg gtgaaagccg tcgtaatgca attagccgtg caatgctgaa agaactgggt      3300
gaactggtta cccgtgttag cagcagccgt gatgttcgtg cagttgttat taccggtgcc      3360
ggtgataaag cattttgtgc cggtgccgat ctgaaagaac gtgcaacaat ggccgaagat      3420
gaagttcgtg catttctgga tggtctgcgt cgtacctttc gtgcaattga aaaaagcgat      3480
tgcgttttta ttgcagccat taatggtgcc gcactgggtg gtggcaccga actggcactg      3540
gcatgtgatc tgcgtgttgc agcaccggca gcagaactgg gtctgaccga agttaaactg      3600
ggcattattc cgggtggtgg tggtacacag cgtctggcac gtctggttgg tccgggtcgt      3660
gcaaaagacc tgattctgac cggcacgtcgt attaatgcag cagaagcatt tagcgttggt      3720
ctggcaaatc gtctggcacc ggaaggtcat ctgctggcag ttgcctatgg tctggcagaa      3780
agcgttgttg aaaatgcacc gattgcagtt gcaaccgcaa aacatgcaat tgatgaaggc      3840
accggtctgg aactggatga tgcactggca ctggaactgc gtaaatatga agaaattctg      3900
aaaaccgaag atcgcctgga aggtctgcgt gcatttgcag aaaaacgtgc accggtttat      3960
aaaggtcgct aataagaacg aaggagatat aatgaaaacc gcacgttggt gtagcctgga      4020
agaagcagtt gcaagcattc cggatggtgc aagcctggca accggtggtt ttatgctggg      4080
tcgtgcaccg atggcactgg ttatggaact gattgcacag ggtaaacgtg atctgggtct      4140
gattagcctg ccgaatccgc tgccagcaga atttctggtt gccggtggtt gtctggctcg      4200
```

-continued

```
tctggaaatt gcatttggtg cactgagtct gcaaggtcgt gttcgtccga tgccgtgtct    4260
gaaacgtgca atggaacagg gcaccctggc atggcgtgaa catgatggtt atcgtgttgt    4320
tcagcgtctg cgtgcagcaa gcatgggtct gccgtttatt ccggcaccgg atgcagatgt    4380
tagcggtctg gcacgtaccg aaccgcctcc gaccgttgaa gatccgttta ccggtctgcg    4440
tgttgcagtt gaaccggcat tttatccgga tgttgcactg ctgcacgcac gtgcagccga    4500
tgaacgtggt aatctgtata tggaagatcc gaccaccgat ctgctggttg cgggtgcagc    4560
aaaacgtgtt attgcaaccg ttgaagaacg tgttgcaaaa ctgcctcgtg caaccctgcc    4620
tggttttcag gttgatcgta ttgttctggc accgggtggt gcactgccga ccggttgtgc    4680
aggtctgtat ccgcatgatg atgaaatgct ggcacgttat ctgagcctgg cagaaaccgg    4740
tcgtgaagcc gaatttctgg aaaccctgct gacccgtcgt gcagcataat gaggatccga    4800
aggagatata catatgagcg caaccctgga tattacaccg gcagaaaccg ttgttagcct    4860
gctggcacgt cagattgatg atggtggtgt tgttgcaacc ggtgttgcaa gtccgctggc    4920
aattctggcc attgcagttg cacgtgccac ccatgcaccg atctgacct atctggcatg    4980 tgttggtagc ctggacccgg aaattccgac cctgctgccg agcagcgaag acctgggtta    5040
tctggatggt cgtagcgcag aaattaccat tccggacctg tttgatcatg cacgtcgtgg    5100
tcgtgttgat accgttttt ttggtgcagc cgaagttgat gccgaaggtc gtaccaatat    5160
gaccgcaagc ggtagtctgg ataaaccgcg taccaaattt ccgggtgttg ccggtgcagc    5220 cacccctgcgt cagtgggttc gtcgtccggt tctgctggtt ccgcgtcaga gccgtcgtaa    5280
tctggttccg gaagttcagg ttgcaaccac ccgtgatccg cgtcgtccgg tgaccctgat    5340
tagcgatctg ggtgtttttg aactgggtgc aagcggtgca cgtctgctgg cacgccatcc    5400
gtgggcaagc gaagaacata ttgcagaacg taccggtttt gcatttcagg ttagcgaagc    5460
actgagcgtt accagcctgc cggatgcacg taccgttgca gcaattcgtg caattgatcc    5520
gcatggctat cgtgatgcac tggttggtgc ataataataa gagagaccag cctgatacag    5580
attaaatcag aacgcagaag cggtctgata aaacagaatt tgcctggcgg cagtagcgcg    5640
gtggtcccac ctgacccat gccgaactca gaagtgaaac gccgtagcgc cgatggtagt    5700
gtggggtcac cccatgcgag agtagggaac tgccaggcat caaataaaac gaaaggctca    5760
gtcgaaagac tgggcctttc gttttatctg ttgtttgtcg gtgaactact agaatttaaa    5820
tagtcaaaag cctccgaccg gaggcttttg actgacactt tgacacaccc tttacccccc    5880
ttataattaa cgtaatagaa ataatttgt ttaactttag gtctctatcg accataatta    5940
attaacttta agaaggagat atacatatga gtcaggcgct aaaaaattta ctgacattgt    6000
taaatctgga aaaaattgag gaaggactct ttcgcgccca gagtgaagat ttaggttac    6060 gccaggtgtt tggcggccag gtcgtgggtc aggccttgta tgctgcaaaa gagacggtcc    6120
ctgaagaacg gctggtacat tcgtttcaca gctactttct tcgccctggc gatagtaaga    6180
agccgattat ttatgatgtc gaaacgctgc gtgacggtaa cagcttcagc gccgccgggg    6240
ttgctgctat tcaaaacggc aaaccgattt tttatatgac tgcctctttc caggcaccag    6300
aagcgggttt cgaacatcaa aaaacaatgc cgtccgcgcc agcgcctgat ggcctccctt    6360
cggaaacgca aatcgcccaa tcgctggcgc acctgctgcc gccagtgctg aaagataaat    6420
tcatctgcga tcgtccgctg gaagtccgtc cggtggagtt tcataaccca ctgaaaggtc    6480
acgtcgcaga accacatcgt caggtgtgga ttcgcgcaaa tggtagcgtg ccggatgacc    6540
```

-continued

```
tgcgcgttca tcagtatctg ctcggttacg cttctgatct taacttcctg ccggtagctc     6600
tacagccgca cggcatcggt tttctcgaac cggggattca gattgccacc attgaccatt     6660
ccatgtggtt ccatcgcccg tttaatttga atgaatggct gctgtatagc gtggagagca     6720
cctcggcgtc cagcgcacgt ggctttgtgc gcggtgagtt ttatacccaa gacggcgtac     6780
tggttgcctc gaccgttcag gaaggggtga tgcgtaatca caattaataa ccatggttat     6840
aagagagacc agcctgatac agattaaatc agaacgcaga agcggtctga taaaacagaa     6900
tttgcctggc ggcagtagcg cggtggtccc acctgacccc atgccgaact cagaagtgaa     6960
acgccgtagc gccgatggta gtgtggggtc accccatgcg agagtaggga actgccaggc     7020
atcaaataaa acgaaaggct cagtcgaaag actgggcctt tcgtttatc tgttgtttgt      7080 cggtgaacta ctagttggcg ggcggccgct tagctctgca gatgagaaat tcttgaagac     7140
gaaagggcct cgtgatacgc ctattttat aggttaatgt catgataata atggtttaag     7200
cttcttagaa tagctcttct atgaggtggc acttttcggg gaaagatatc cgcatatatg     7260
gtgcactctc agtacaatct gctctgatgc cgcatagtta agccagtata cactccgcta     7320
tcgctacgtg actgggtcat ggctgcgccc cgacacccgc caacacccgc tgacgcgccc     7380
tgacgggctt gtctgctccc ggcatccgct tacagacaag ctgtgaccgt ctccgggagc     7440
tgcatgtgtc agaggttttc accgtcatca ccgaaacgcg cgaggcagct gcggtaaagc     7500
tcatcagcgt ggtcgtgaag cgattcacag atgtctgcct gttcatcggt acctttcatg     7560
atatatctcc caatttgtgt agggcttatt atgcacgctt aaaaataata aaagcagact     7620
tgacctgata gtttggctgt gagcaattat gtgcttagtg catctaacgc ttgagttaag     7680
ccgcgccgcg aagcggcgtc ggcttgaacg aattgttaga cattatttgc cgactacctt     7740
ggtgatctcg cctttcacgt agtggacaaa ttcttccaac tgatctgcgc gcgaggccaa     7800
gcgatcttct tcttgtccaa gataagcctg tctagcttca agtatgacgg gctgatactg     7860
ggccggcagg cgctccattg cccagtcggc agcgacatcc ttcggcgcga ttttgccggt     7920
tactgcgctg taccaaatgc gggacaacgt aagcactaca tttcgctcat cgccagccca     7980
gtcgggcggc gagttccata gcgttaaggt ttcatttagc gcctcaaata gatcctgttc     8040
aggaaccgga tcaaagagtt cctccgccgc tggacctacc aaggcaacgc tatgttctct     8100
tgcttttgtc agcaagatag ccagatcaat gtcgatcgtg gctggctcga agatacctgc     8160
aagaatgtca ttgcgctgcc attctccaaa ttgcagttcg cgcttagctg gataacgcca     8220
cggaatgatg tcgtcgtgca caacaatggt gacttctaca gcgcggagaa tctcgctctc     8280
tccaggggaa gccgaagttt ccaaaaggtc gttgatcaaa gctcgccgcg ttgtttcatc     8340
aagccttacg gtcaccgtaa ccagcaaatc aatatcactg tgtggcttca ggccgccatc     8400
cactgcggag ccgtacaaat gtacggccag caacgtcggt tcgagatggc gctcgatgac     8460
gccaactacc tctgatagtt gagtcgatac ttcggcgatc accgcttccc tcatgatgtt     8520
taactttgtt ttagggcgac tgccctgctg cgtaacatcg ttgctgctcc ataacatcaa     8580
acatcgaccc acggcgtaac gcgcttgctg cttggatgcc cgaggcatag actgtacccc     8640
aaaaaaacag tcataacaag ccatgaaaac cgccacgagc tcctgtcaga ccaagtttac     8700
gagctcgctt ggactcctgt tgatagatcc agtaatgacc tcagaactcc atctggattt     8760
```

-continued

```
gttcagaacg ctcggttgcc gccgggcgtt ttttattggt gagaatccaa gcactaggga   8820
cagtaagacg ggtaagcctg ttgatgatac cgctgcctta ctgggtgcat tagccagtct   8880
gaatgacctg tcacgggata atccgaagtg gtcagactgg aaaatcagag ggcaggaact   8940
gctgaacagc aaaaagtcag atagcaccac atagcagacc cgccataaaa cgccctgaga   9000
agcccgtgac gggctttct tgtattatgg gtagtttcct tgcatgaatc cataaaaggc     9060
gcctgtagtg ccatttaccc ccattcactg ccagagccgt gagcgcagcg aactgaatgt   9120
cacgaaaaag acagcgactc aggtgcctga tggtcggaga caaaaggaat attcagcgat   9180
ttgcccgagc ttgcgagggt gctacttaag cctttagggt tttaaggtct gttttgtaga   9240
ggagcaaaca gcgtttgcga catcctttg taatactgcg gaactgacta aagtagtgag    9300
ttatacacag ggctgggatc tattcttttt atcttttttt attctttctt tattctataa   9360
attataacca cttgaatata aacaaaaaaa acacacaaag gtctagcgga atttacagag   9420
ggtctagcag aatttacaag ttttccagca aaggtctagc agaatttaca gatacccaca   9480
actcaaagga aaaggacatg taattatcat tgactagccc atctcaattg gtatagtgat   9540
taaaatcacc tagaccaatt gagatgtatg tctgaattag ttgtttttcaa agcaaatgaa  9600 ctagcgatta gtcgctatga cttaacggag catgaaacca agctaatttt atgctgtgtg   9660
gcactactca accccacgat tgaaaaccct acaaggaaag aacggacggt atcgttcact   9720
tataaccaat acgctcagat gatgaacatc agtagggaaa atgcttatgg tgtattagct   9780
aaagcaacca gagagctgat gacgagaact gtggaaatca ggaatccttt ggttaaaggc   9840
tttgagattt tccagtggac aaactatgcc aagttctcaa gcgaaaaatt agaattagtt   9900
tttagtgaag agatattgcc ttatctttc cagttaaaaa aattcataaa atataatctg    9960
gaacatgtta agtcttttga aaacaaatac tctatgagga tttatgagtg gttattaaaa   10020
gaactaacac aaaagaaaac tcacaaggca aatatagaga ttagccttga tgaatttaag   10080
ttcatgttaa tgcttgaaaa taactaccat gagtttaaaa ggcttaacca atgggttttg    10140
aaaccaataa gtaaagattt aaacacttac agcaatatga aattggtggt tgataagcga   10200
ggccgcccga ctgatacgtt gattttccaa gttgaactag atagacaaat ggatctcgta   10260
accgaacttg agaacaacca gataaaaatg aatggtgaca aaataccaac aaccattaca    10320
tcagattcct acctacgtaa cggactaaga aaaacactac acgatgcttt aactgcaaaa    10380
attcagctca ccagtttga ggcaaaattt ttgagtgaca tgcaaagtaa gcatgatctc     10440
aatggttcgt tctcatggct cacgcaaaaa caacgaacca cactagagaa catactggct    10500
aaatacggaa ggatctgagg ttcttatggc tcttgtatct atcagtgaag catcaagact    10560
aacaaacaaa agtagaacaa ctgttcaccg ttagatatca aagggaaaac tgtccataag   10620
cacagatgaa aacggtgtaa aaaagataga tacatcagag cttttacgag ttttttggtgc  10680 atttaaagct gttcaccatg aacagatcga caatgtaacg catgcaccga gcgcagcgag   10740
tcagtgagcg aggaagcgga acagcgcctg                                    10770
```

MEANS AND METHODS FOR PRODUCING ISOBUTENE FROM 3-METHYLCROTONIC ACID

CROSS-REFERENCE TO RELATED APPLICATIONS

This application is a § 371 National Stage Application of PCT/EP2021/086687 filed on Dec. 20, 2021, which claims priority to EP 20215872.1 filed on Dec. 21, 2020, both of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Dec. 7, 2023, and is named GB-35-US_Sequence_Listing.txt and is 14,488 bytes in size.

The present invention relates to a method for the production of isobutene from a carbon source characterized in that it comprises (a) culturing a microorganism capable of producing 3-methylcrotonic acid from a carbon source in a liquid culture medium, thereby producing said 3-methylcrotonic acid so that it accumulates in the liquid culture medium; and (b) enzymatically converting said 3-methylcrotonic acid contained in the liquid culture medium obtained in step (a) into isobutene by: (i) incubating a microorganism expressing an FMN-dependent decarboxylase associated with an FMN prenyl transferase with said liquid culture medium containing 3-methylcrotonic acid obtained in step (a); and/or (ii) incubating an FMN-dependent decarboxylase associated with an FMN prenyl transferase with said liquid culture medium containing 3-methylcrotonic acid obtained in step (a); thereby producing said isobutene; and (c) recovering the produced isobutene.

A large number of chemical compounds are currently derived from petrochemicals. Alkenes (such as ethylene, propylene, the different butenes, or else the pentenes, for example) are used in the plastics industry, for example for producing polypropylene or polyethylene, and in other areas of the chemical industry and that of fuels. Butylene exists in four forms, one of which, isobutene (also referred to as isobutylene), enters into the composition of methyl-tert-butyl-ether (MTBE), an anti-knock additive for automobile fuel. Isobutene can also be used to produce isooctene, which in turn can be reduced to isooctane (2,2,4-trimethylpentane); the very high octane rating of isooctane makes it the best fuel for so-called "gasoline" engines. Alkenes such as isobutene are currently produced by catalytic cracking of petroleum products (or by a derivative of the Fischer-Tropsch process in the case of hexene, from coal or gas). The production costs are therefore tightly linked to the price of oil. Moreover, catalytic cracking is sometimes associated with considerable technical difficulties which increase process complexity and production costs.

The production by a biological pathway of alkenes such as isobutene is called for in the context of a sustainable industrial operation in harmony with geochemical cycles. The first generation of biofuels consisted in the fermentative production of ethanol, as fermentation and distillation processes already existed in the food processing industry.

The production of second generation biofuels is in an exploratory phase, encompassing in particular the production of long chain alcohols (butanol and pentanol), terpenes, linear alkanes and fatty acids. Two recent reviews provide a general overview of research in this field: Ladygina et al.

(Process Biochemistry 41 (2006), 1001) and Wackett (Current Opinions in Chemical Biology 21 (2008), 187). The conversion of isovalerate to isobutene by the yeast *Rhodotorula minuta* has been described (Fujii et al. (Appl. Environ. Microbiol. 54 (1988), 583)).

Gogerty et al. (Appl. Environm. Microbiol. 76 (2010), 8004-8010) and van Leeuwen et al. (Appl. Microbiol. Biotechnol. 93 (2012), 1377-1387) describe the production of isobutene from acetoacetyl-CoA by enzymatic conversions wherein the last step of the proposed pathway is the conversion of 3-hydroxy-3-methylbutyric acid (also referred to as 3-hydroxyisovalerate (HIV)) by making use of a mevalonate diphosphate decarboxylase. This reaction for the production of isobutene from 3-hydroxy-3-methylbutyric acid is also described in WO2010/001078 which, in general terms, describes methods for generating alkenes through a biological process, in particular methods for producing terminal alkenes (in particular propylene, ethylene, 1-butylene, isobutylene or isoamylene) from molecules of the 3-hydroxyalkanoate type.

WO2012/052427 also describes a method for generating alkenes through a biological process while, in particular, a method for producing alkenes (for example propylene, ethylene, 1-butylene, isobutylene or isoamylene) from molecules of the 3-hydroxyalkanoate type is described. In this context, the reaction for the production of isobutene from 3-hydroxy-3-methylbutyric acid is also described in WO2012/052427. WO 2016/042012 describes methods for producing said 3-hydroxy-3-methylbutyric acid. In particular, WO 2016/042012 describes methods for producing 3-hydroxy-3-methylbutyric acid comprising the step of enzymatically converting 3-methylcrotonyl-CoA into 3-methylcrotonic acid and the step of enzymatically further converting the thus produced 3-methylcrotonic acid into 3-hydroxy-3-methylbutyric acid.

In Gogerty et al. (loc. cit.) and in van Leeuwen et al. (loc. cit.) the production of 3-hydroxy-3-methylbutyric acid is proposed to be achieved by the conversion of 3-methylcrotonyl-CoA via 3-hydroxy-3-methylbutyryl-CoA. In order to further improve the efficiency and variability of methods for producing isobutene from renewable resources, alternative routes for the provision of isobutene and its precursors have been developed by providing methods for the production of isobutene comprising the enzymatic conversion of 3-methylcrotonic acid (also termed 3-methyl-2-butenoic acid, 3,3-dimethylacrylic acid or senecioic acid) into isobutene.

In particular, in WO 2017/085167, methods for the production of isobutene have been described comprising the enzymatic conversion of 3-methylcrotonic acid into isobutene, wherein the enzymatic conversion of 3-methylcrotonic acid into isobutene is achieved by making use of an FMN-dependent decarboxylase associated with an FMN prenyl transferase, wherein said FMN prenyl transferase catalyzes the prenylation of a flavin cofactor (FMN or FAD) utilizing dimethylallyl phosphate (DMAP) into a flavin-derived cofactor while these enzymes have artificially been implemented in a pathway which ultimately leads to the production of isobutene. Moreover, in WO 2017/085167, methods have been described, wherein such a method further comprises (a) providing the 3-methylcrotonic acid by the enzymatic conversion of 3-methylcrotonyl-CoA into 3-methylcrotonic acid, or (b) providing the 3-methylcrotonic acid by the enzymatic conversion of 3-hydroxyisovalerate (HIV) into 3-methylcrotonic acid.

WO 2017/085167 also describes that this method which has been developed for the production of isobutene from 3-methylcrotonyl-CoA via 3-methylcrotonic acid or from 3-hydroxyisovalerate (HIV) via 3-methylcrotonic acid may be embedded in a pathway for the production of isobutene starting from acetyl-CoA which is a central component and an important key molecule in metabolism used in many biochemical reactions. The corresponding reactions are schematically shown in FIG. 1.

In WO 2018/206262 it is described that 3-methylcrotonic acid is enzymatically converted into isobutene by making use of an FMN-dependent decarboxylase associated with an FMN prenyl transferase when dimethylallyl pyrophosphate (DMAPP) instead of DMAP is used.

WO 2018/206262, moreover, describes that the enzymatic conversion of 3-methylcrotonic acid into isobutene which is achieved by making use of an FMN-dependent decarboxylase associated with an FMN prenyl transferase, wherein said FMN prenyl transferase catalyzes the prenylation of a flavin cofactor (FMN or FAD) utilizing dimethylallyl phosphate (DMAP) and/or dimethylallyl pyrophosphate (DMAPP) into a flavin-derived cofactor is a key step of the above overall metabolic pathway from acetyl-CoA into isobutene. It has been found that in this key step, the availability of dimethylallyl phosphate (DMAP) and/or dimethylallyl pyrophosphate (DMAPP) as well as the availability of the flavin cofactor FMN are limiting factors while in WO 2018/206262 improved methods by increasing the pool/amount of dimethylallyl phosphate (DMAP) and/or dimethylallyl pyrophosphate (DMAPP) in order to ensure the efficient biosynthesis of the prenylated flavin cofactor (FMN or FAD) are described. Moreover, WO 2020/188033 is based on the concept of increasing the yield of isobutene by providing and maintaining a high pool of acetyl-CoA in a cells used for isobutene production wherein the acetyl-CoA pool is kept high by ensuring an increased uptake of pantothenate by the cell and/or an increased conversion of pantothenate into CoA. Accordingly, WO 2020/188033, inter alia, describes a recombinant organism or microorganism which is capable of enzymatically converting acetyl-CoA into isobutene, (A) wherein in said organism or microorganism: (i) acetyl-CoA is enzymatically converted into acetoacetyl-CoA, (ii) acetoacetyl-CoA is enzymatically converted into 3-hydroxy-3-methylglutaryl-CoA, (iii) 3-hydroxy-3-methylglutaryl-CoA is enzymatically converted into 3-methylglutaconyl-CoA, (iv) 3-methylglutaconyl-CoA is enzymatically converted into 3-methylcrotonyl-CoA, and (v) wherein said 3-methylcrotonyl-CoA is converted into isobutene by: (a) enzymatically converting 3-methylcrotonyl-CoA into 3-methylcrotonic acid which is then further enzymatically converted into said isobutene; or (b) enzymatically converting 3-methylcrotonyl-CoA into 3-hydroxy-3-methylbutyryl-CoA which is then further enzymatically converted into 3-hydroxy-3-methylbutyric acid which is then further enzymatically converted into 3-phosphonoxy-3-methylbutyric acid which is then further enzymatically converted into said isobutene; (B) wherein said recombinant organism or microorganism has an increased pool of coenzyme A (CoA) over the organism or microorganism from which it is derived due to: (i) an increased uptake of pantothenate; and/or (ii) an increased conversion of pantothenate into CoA.

Further, WO 2014/086780 describes a fermentation method for producing a hydrocarbon compound, preferably isobutene, comprising the culturing of an organism in a liquid fermentation medium, wherein said organism produces a desired hydrocarbon compound by an enzymatic pathway, said enzymatic pathway comprising an intermediate which evaporates into the gaseous phase and wherein said intermediate is recovered from the gaseous phase and is reintroduced into the liquid fermentation medium.

Moreover, WO 2014/086781 describes a process for the fermentative production of a hydrocarbon, preferably isobutene, wherein a microorganism producing the hydrocarbon is cultured in a liquid fermentation medium in a fermenter, wherein an inlet gas comprising oxygen is fed into the fermenter and the total pressure of the inlet gas before introduction into the fermenter is about 1.5 bar to about 15 bar (about 150 kPa to about 1500 kPa), wherein the hydrocarbon is obtained in a gaseous state in the fermentation off-gas, and wherein the concentration of oxygen in the fermentation off-gas is controlled to be below about 10 vol-%.

Although, as described above, various approaches have been described in the prior art for producing isobutene by enzymatic conversions in biological systems and in fermentation processes/fermenters, thereby allowing to use renewable resources as raw material, there is still a need for improvements, in particular, regarding efficiency, effectiveness and safety of such (fermentation) methods in order to increase yield and/or safety and to make them commercially more attractive.

The present invention meets this demand by providing, in a first aspect, a method for the production of isobutene from a carbon source characterized in that it comprises:

(a) culturing a microorganism capable of producing 3-methylcrotonic acid from a carbon source in a liquid culture medium, thereby producing said 3-methylcrotonic acid so that it accumulates in the liquid culture medium; and (b) enzymatically converting said 3-methylcrotonic acid contained in the liquid culture medium obtained in step (a) into isobutene by:

(i) incubating a microorganism expressing an FMN-dependent decarboxylase associated with an FMN prenyl transferase with said liquid culture medium containing 3-methylcrotonic acid obtained in step (a); and/or (ii) incubating an FMN-dependent decarboxylase associated with an FMN prenyl transferase with said liquid culture medium containing 3-methylcrotonic acid obtained in step (a);

thereby producing said isobutene; and (c) recovering the produced isobutene.

In a second aspect, the present invention provides a method for the production of isobutene from a carbon source characterized in that it comprises:

(a) culturing a microorganism capable of producing 3-methylcrotonic acid from a carbon source in a liquid culture medium, thereby producing said 3-methylcrotonic acid so that it accumulates in the liquid culture medium; and (b) thermochemically converting said 3-methylcrotonic acid contained in the liquid culture medium obtained in step (a) into isobutene, preferably at a temperature between 180° C. and 400° C.; and (c) recovering the produced isobutene.

So far contemplated, fermentative methods for producing isobutene from 3-methylcrotonic acid (also sometimes referred to as prenate herein) are based on conventional fermentation methods using microorganisms which are able to produce isobutene. The isobutene, which is produced under normal fermentation conditions as a gaseous compound, is recovered as part of the off-gas of the culture which is a mixture of various gases which are part of the inlet gas used for ventilation of the culture during cultivation or which are produced during culture. It was found that under such conditions, the percentage of isobutene in the off-gas of the culture normally only reaches amounts of about 3 to 7 mol %. Thus, a considerable amount of time and effort is involved in order to purify the isobutene from the off-gas to the desired degree of purity.

The present inventors made the surprising finding that the amount/percentage of isobutene in the off-gas of a fermentation method comprising the biological conversion leading from 3-methylcrotonic acid to isobutene can be dramatically increased if the enzymatic reactions leading to the production of 3-methylcrotonic acid and the subsequent enzymatic conversion of 3-methylcrotonic acid into isobutene are uncoupled in the sense that it is first ensured that 3-methylcrotonic acid is produced during fermentation from a carbon source and is accumulated in the culture medium (and not directly converted into isobutene) and that only after accumulation of the 3-methylcrotonic acid in the culture medium the 3-methylcrotonic acid is subsequently, in a separate reaction, converted into isobutene. This second step of converting 3-methylcrotonic acid into isobutene can be achieved under simplified conditions and does not require the maintenance of fermentation conditions. It is sufficient in this second step to bring an enzyme which allows the conversion of 3-methylcrotonic acid into contact with the accumulated 3-methylcrotonic acid or cells of a microorganism which produces such an enzyme. It was found that the mere incubation of the solution containing the accumulated 3-methylcrotonic acid and the enzyme/microorganism leads to an extremely efficient conversion of 3-methylcrotonic acid into isobutene and an extremely high percentage of isobutene in the off-gas of the incubation reaction. Moreover, it could be shown that it is advantageous if the incubation step in which the 3-methylcrotonic acid is converted into isobutene is carried out in a vessel with no gas supply at all or a very low gas supply.

As shown in the Examples below, the claimed method allows to efficiently convert 3-methylcrotonic acid (prenate) into isobutene and to, thus, lead to an efficient production of isobutene. Moreover, the Examples show that when gas supply is kept low (i.e., <0.1 vvm) or no gas is supplied (0 vvm) during the incubation step used for the conversion of 3-methylcrotonic acid into isobutene, the produced isobutene (IBN) concentrations are particularly high in the off-gas. Accordingly, it is easier to purify the isobutene to the desired degree of purity.

As shown in the Examples, when using conditions of low gas supply during the incubation step in which 3-methylcrotonic acid is converted into isobutene, isobutene and $CO_2$ (which is produced during the enzymatic decarboxylation of 3-methylcrotonic acid into isobutene) are produced at high concentrations and, in fact, basically only $CO_2$ and isobutene are produced when the gas supply is kept extremely low during the incubation step.

Whenever reference is made to 3-methylcrotonic acid, both, its deprotonated carboxylate ion form (i.e., the COO⁻ form, namely, 3-methylcrotonate) as well as its protonated acidic form (i.e., the COOH form, namely methylcrotonic acid) are meant. In fact, its form depends on the pH of the solution and, accordingly, the definition of 3-methylcrotonic acid interchangeably denotes either form, i.e., 3-methylcrotonate as well as 3-methylcrotonic acid.

When present as salt form, namely as 3-methylcrotonate, the preferred cation is $Na^+$, $Ca^{2+}$, $Mg^{2+}$, $K^+$ or $NH^{4+}$.

The method according to the present invention comprises in step (a) the culturing of a microorganism which is capable of producing 3-methylcrotonic acid from a carbon source in a liquid culture medium, thereby producing said 3-methylcrotonic acid so that it accumulates in the liquid culture medium.

The term "culturing" as used in this context refers to the keeping the cells in a liquid medium, thereby keeping them vital and allowing the production of the required enzymes for the production of the desired product(s). Preferably, the term "culturing" also encompasses the growing of microorganism cells under conditions that allow their propagation, proliferation and cell division, thereby increasing the number of the cells in the liquid culture medium. Thus, the term "culturing" refers to maintaining the microorganism in culture conditions which allow for the survival of cells as well as for the occurrence of the metabolic processes which are required for the cells so as to convert the carbon source into 3-methylcrotonic acid. Such conditions generally comprise the provision of cells with a carbon source in the culture medium, agitation of the culture medium, maintaining the temperature of the culture medium at a value which allows for the required metabolic conversions to occur (and, if desired, of the growth of the microorganism) and supplying the cultured cells with air or a gas mixture which allows survival and metabolic activity of the cells.

Thus, the term "culturing" as used in this context is to be understood as a "fermentation", i.e. a metabolic process that produces chemical changes in organic substrates, preferably through the action of enzymes and, accordingly, refers to a process wherein products are synthesized from growth substrates via the microorganisms' native or genetically modified metabolism and are accomplished by metabolic intermediates. Therefore, the term culturing makes possible the occurrence of metabolism of the cultured cells, their growth and their survival. Moreover, the cultivation step, in order to allow this, requires carbon and energy sources to be present (e.g. in the form of glucose and oxygen).

In general, the culturing step (a) of the method according to the present invention can be carried out in terms of a classical fermentation method using means (like fermenters and their equipment) and methods well-known in the art, with the culture medium and the culture conditions adapted to the specific microorganism employed in step (a).

The term "a microorganism capable of producing 3-methylcrotonic acid from a carbon source" refers to a microorganism which is capable, when cultured under suitable conditions, to express enzymes which allow the conversion of the respective carbon source into 3-methylcrotonic acid and which, thus, produces 3-methylcrotonic acid from the carbon source during culturing.

Methods for the enzymatic production of 3-methylcrotonic acid from a carbon source are known in the art and (recombinant) microorganisms capable of catalyzing the respective enzymatic conversions have been described. In principle, any microorganism which is capable of converting a carbon source into 3-methylcrotonic acid can be employed in step (a) of the method of the present invention.

Only as examples, without being limited thereto, possible individual steps of enzymatic conversions starting from a carbon source into 3-methylcrotonic acid are described further below. Moreover, in preferred embodiments, as further examples, without being limited thereto, possible individual steps of enzymatic conversions starting from a carbon source which gives rise to the central metabolite acetyl-CoA and further to 3-methylcrotonic acid are described further below.

Moreover, the term "a microorganism capable of producing 3-methylcrotonic acid from a carbon source" means, in the context of the present invention, that such a microorganism does not or not to a substantial extent further metabolize or convert the produced 3-methylcrotonic acid into other compounds, in particular to isobutene, under the applied culture conditions. This term in particular means that the microorganism does not convert the produced 3-methylcrotonic acid into isobutene during the culturing step (a). This can be due to the fact that the microorganism employed in step (a) of the method according to the present invention does not comprise the genetic information encoding an enzyme which can convert 3-methylcrotonic acid into isobutene and, thus, is not able to produce an enzyme which can catalyze this reaction.

Alternatively, the microorganism employed in step (a) may also be a microorganism which comprises the genetic information encoding an enzyme which can convert 3-methylcrotonic acid into isobutene but which does not express this enzyme under the culturing conditions used in step (a). For example, the gene encoding a corresponding enzyme may be placed under the control of a promoter the activity of which can be regulated and which is inactive under the culture conditions used in step (a).

In a preferred embodiment, the microorganism employed in step (a) of the method according to the present invention is a microorganism which does not comprise a gene coding for an enzyme which can convert 3-methylcrotonic acid into isobutene.

However, it is also possible to employ in step (a) of the method of the present invention a microorganism which naturally comprises a gene which encodes for an enzyme which can in principle convert 3-methylcrotonic acid into isobutene, such as an FMN-dependent decarboxylase associated with an FMN prenyl transferase, but in which the activity of this enzyme to convert 3-methylcrotonic acid into isobutene is so low that there does not occur any substantial conversion during the cultivation step (a).

The 3-methylcrotonic acid which is produced by the microorganism during the culturing of step (a) of the method according to the present invention accumulates in the culture medium.

Thus, the culturing of step (a) is carried out for a sufficient time so as to allow the conversion of the carbon source into 3-methylcrotonic acid and its accumulation in the culture medium. Preferably, the culturing is carried out until the carbon source provided in the culture medium is metabolized by the cells (i.e., depleted from the culture medium) to at least 20%, 30%, 40%, 50% or 60%, preferably at least 70%, more preferably at least 80%, even more preferably at least 90%, or at least 95%, particularly preferred at least 99%.

"Accumulates" means that the 3-methylcrotonic acid which is produced by the microorganism in step (a) occurs mainly in the culture medium and that its concentration increases during the culturing in step (a). Preferably, the culturing is carried out until no further increase in the concentration of 3-methylcrotonic acid can be observed.

It is also preferable that the culturing of step (a) is carried out until a concentration of at least 5 g/l more preferable of at least 10 g/l, even more preferable of at least 20 g/l and even more preferable of at least 40 g/l of 3-methylcrotonic acid is achieved in the liquid culture medium.

Once the desired accumulation of 3-methylcrotonic acid in the culture medium is achieved in step (a) of the method of the present invention, the culturing of the microorganisms is stopped. Stopping the culturing means that measures are stopped which are used in fermentative methods to maintain growth of the bacteria.

The culturing is preferably stopped when carbon source consumption is low (preferably, lower than 0.03 g of carbon source/g of DCW (dry cell weight)/hour) and/or 3-methylcotonic acid production rate is low (preferably, lower than 0.01 g of 3-methylcotonic acid/g of DCW/hour).

The carbon source consumption and 3-methycrotonic acid production, respectively, can be measured by the methods known in the art, e.g., by HPLC.

The culturing can also preferably be stopped when undesirable by-products (for example, organic acids like acetic acid, lactic acid, or alcohols like ethanol) start to be accumulated in the culture medium. The accumulation of by-products in a culture can be measured by methods known in the art (e.g., by HPLC or GC analysis).

Preferably, the culturing can be stopped by terminating the aeration and/or the provision of the carbon source.

Thus, at the end of the culturing step (a) of the method according to the present invention a liquid culture medium is obtained which comprises the accumulated 3-methylcrotonic acid and the microorganism used for producing it. This liquid culture medium is subsequently used in the incubation step (b) of the method according to the present invention.

According to step (b) of the method according to the present invention, the 3-methylcrotonic acid produced in step (a) and contained in the liquid culture medium is subsequently enzymatically converted into isobutene.

This step is characterized in that it does not require the cultivation of a microorganism but can be achieved by simply incubating the 3-methylcrotonic acid produced in step (a) with an enzyme which can convert 3-methylcrotonic acid into isobutene (in particular with an FMN-dependent decarboxylase associated with an FMN prenyl transferase) or with (a pre-grown culture of) a microorganism producing such an enzyme. That no cultivation is effected in this step (b) means, e.g., that generally no further nutrients are added. Incubation merely requires that the substrate (3-methylcrotonic acid) and the enzyme (either in the form of an isolated enzyme or in the form of a microorganism which had been precultured and which synthesized the enzyme) are brought into contact and incubated under controlled reactions conditions (e.g. temperature and pH value) which allow for the enzymatic conversion of 3-methylcrotonic acid into isobutene.

While the culturing of step (a) can be stopped as described above, the incubation can be started by bringing together the liquid culture medium containing the 3-methylcotonic acid with the cells expressing FMN-dependent decarboxylase associated with an FMN prenyl transferase or with FMN-dependent decarboxylase associated with an FMN prenyl transferase.

Thus, the term "incubating" as used in step (b) of the method of the present invention does not necessarily require the microorganism, if employed in this step, to be kept vital. The term "incubating" does also not necessarily encompass the further proliferation/growth of a microorganism employed in step (b). "Incubation" in terms of the present invention refers to the maintaining of the microorganism expressing the desired enzymes and the enzymes, respectively, in an active state, preferably under optimal temperature, humidity and other conditions that allow conversion of 3-methylcrotonic acid into isobutene. Thus, "incubation" in terms of the present invention, in contrast to the "culturing"/ "fermentation" of step (a), merely refers, in essence, to the conversion of 3-methylcrotonic acid into isobutene while the proliferation/growth of a microorganism and/or the production of the respective enzymes required for the conversion of 3-methylcrotonic acid into isobutene is not necessarily required. Accordingly, in the "incubation" of step (b) of the method of the present invention, a proliferation/growth of a microorganism and/or a production of the respective enzymes required for the conversion of 3-methylcrotonic acid into isobutene, if at all encompassed or required, is physically separated from the actual conversion of 3-methylcrotonic acid into isobutene. In contrast, in the above "culturing", the steps from a carbon source to 3-methylcrotonic acid are linked as described in more detail further below.

The incubation step (b) of the method according to the present invention is carried out in a vessel which comprises a solution containing the 3-methylcrotonic acid produced in step (a) and the enzyme or microorganism expressing the enzyme for the converting the 3-methylcrotonic acid into isobutene.

The vessel is designed as a closed system so as to allow the control of the flow of gas out of the vessel and, optionally, also the flow of the gas into the vessel.

The vessel may also be equipped with means for allowing agitation of the solution contained in the vessel or means for controlling the temperature during the incubation step (b).

Without being bound to theory, agitation allows the mixing of cells/enzymes and the solution containing 3-methylcrotonic acid and, accordingly, the equal distribution of the cells and/or the enzymes and the 3-methylcrotonic acid in the solution. Moreover, agitation may facilitate the exit of gaseous components, such as isobutene, from the solution into the gaseous phase.

Advantageously, in a preferred embodiment, the vessel comprises a pH regulation system and/or a connection to a storage tank of acid which is used to regulate/adjust the pH of the liquid culture medium in the vessel. As an example, sulfuric acid or phosphoric acid may be used to regulate/adjust the pH.

In another preferred embodiment, the vessel can be fed during the incubation step (b) with a (concentrated) solution of 3-methylcrotonic acid (or a salt thereof), preferably with 3-methylcrotonic acid, which had been produced in accordance with step (a) of the method according to the present invention. Possible ways of feeding 3-methylcrotonic acid into the solution are described below. By feeding 3-methylcrotonic acid into the vessel during the incubation step (b), it is, e.g. possible to maintain the concentration of 3-methylcrotonic acid in the medium at a desired level which allows an efficient conversion into isobutene. Thus, in such an embodiment it is also envisaged that the concentration of 3-methylcrotonic acid in the medium is monitored (e.g. constantly or at pre-determined time intervals) and the concentration is adjusted to a desired concentration by feeding additional 3-methylcrotonic acid into the medium.

In one embodiment of the present invention, the incubation step (b) is carried out in a vessel which is designed as a closed system and which only allows a controlled efflux of gas through an outlet but which does not allow an influx of gas. A corresponding vessel is schematically shown in the upper part of FIG. 4. Thus, in such an embodiment, there is no gas supply from the outside and the method is carried out in a vessel without gas supply. In this case the gas (including isobutene) produced during the incubation step (b) is captured as an off-gas through an outlet which allows the efflux of gas. Thus, in such a closed system, the gas produced during the incubation of step (b) of the present invention can be recovered from the vessel without re-supplementing the corresponding volume of gas with an inlet gas. In other words, when gas (including isobutene) is produced during the incubation the pressure increases in the vessel due to its production. To maintain constant pressure, gas can be recovered from the vessel via an outlet.

Accordingly, in such a situation, the vessel is a closed system (apart from the gas outlet) and the pressure in the vessel is preferably controlled in a way that it is not increased (i.e., by allowing a gas efflux via an outlet).

It is shown in the appended Examples that such an incubation without any gas supply at all during the incubation step (b) leads to the production of a gas with an extremely high content of isobutene.

In another embodiment, the incubation step (b) is carried out in a vessel which is designed as a closed system but which allows the controlled efflux of gas and the controlled influx of gas. In such an embodiment, an inlet gas can be provided to the system in a controlled manner and the inlet gas can be used to force the gas produced by the incubation which contains isobutene out of the system. A corresponding vessel is schematically illustrated in the lower part of FIG. 4.

Accordingly, there is an inlet via which inlet gas (like, e.g., nitrogen, air, etc. as outlined in more detail further below) can be supplied in a controlled manner. Moreover, there is an outlet to allow the efflux of gas.

It is preferred in such a situation that the flux of the inlet gas (the gas supply) is kept at a low rate. Preferably, the flux is kept at a rate of less than 0.1 vvm (vessel volume per minute).

The unit "vvm" (which stands for "vessel volume per minute") is known to the person skilled in the art. The unit "vvm" is the volume of inlet gas flow under reference conditions (101.325 kPa, 0° C.) per volume of liquid fermentation medium per minute and can easily be adjusted in a vessel. Corresponding devices are known to the skilled person.

In preferred embodiments, the gas supply is in the range from >0.0 to 0.1 vvm, >0.0 to 0.09 vvm, >0.0 to 0.08 vvm, >0.0 to 0.07 vvm, >0.0 to 0.06 vvm, >0.0 to 0.05 vvm, >0.0 to 0.04 vvm, >0.0 to 0.03 vvm, >0.0 to 0.02 vvm, or >0.0 to 0.01 vvm. In a more preferred embodiment, the gas supply is in the range from >0.0 to 0.05 vvm.

In further preferred embodiments, the gas supply is <0.09 vvm, <0.08 vvm, <0.07 vvm, <0.06 vvm, <0.05 vvm, <0.04 vvm, <0.03 vvm, <0.02 vvm, <0.01 vvm or <0.005 vvm. In a more preferred embodiment, the gas supply is <0.05 vvm.

In a particularly preferred embodiment, the gas supply is <0.1 vvm. In another particularly preferred embodiment, the gas supply is <0.05 vvm. In another particularly preferred embodiment, the gas supply is <0.02 vvm.

The gas can be supplied to the vessel via an inlet to the solution (by, e.g., blowing gas through the solution). Alternatively, the gas can also be supplied to the gas phase of the vessel.

Preferably, the inlet gas is provided to the solution in the vessel with a sparger (by, e.g., "blowing" the gas through the solution) from the bottom of the vessel.

It is shown in the appended Examples that such an incubation with only a low gas supply during the incubation step (b) leads to the production of a gas with a very high content of isobutene. In particular, the Examples show that when the incubation step is carried out with no or low gas supply, $CO_2$ and isobutene are produced at high concentrations and, in fact, basically only $CO_2$ and isobutene are produced. In consequence, the outlet gas from the vessel, as explained in more detail further below, predominantly or even exclusively (with the exception of eventual trace amounts of other gases) consists of $CO_2$ and isobutene while basically no oxygen is present.

The method of the present invention is, therefore, also advantageous in that it can eliminate or at least greatly reduce the risk of combustion of the outlet gas produced during the production of isobutene. Accordingly, if there is no gas supply, or if the gas supply is controlled at a low level, the oxygen in the outlet gas is below about 10 vol % and, thus, below the minimum oxygen concentration (MOC) of isobutene required for combustion. Accordingly, the method of the present invention also allows to improve the safety of the production of isobutene and facilitates subsequent processing of the recovered outlet gas.

The inlet gas is preferably air, inert gas, a mixture of several gases or a mixture of air and inert gas, wherein said inert gas is preferably selected from nitrogen, helium, argon, neon, $CO_2$ and a mixture of these gases.

Moreover, if nitrogen (or another inert gas) is used in the gas supply, it can inert the system (thereby avoiding/reducing the risk of combustion and/or explosion).

Figure 9:
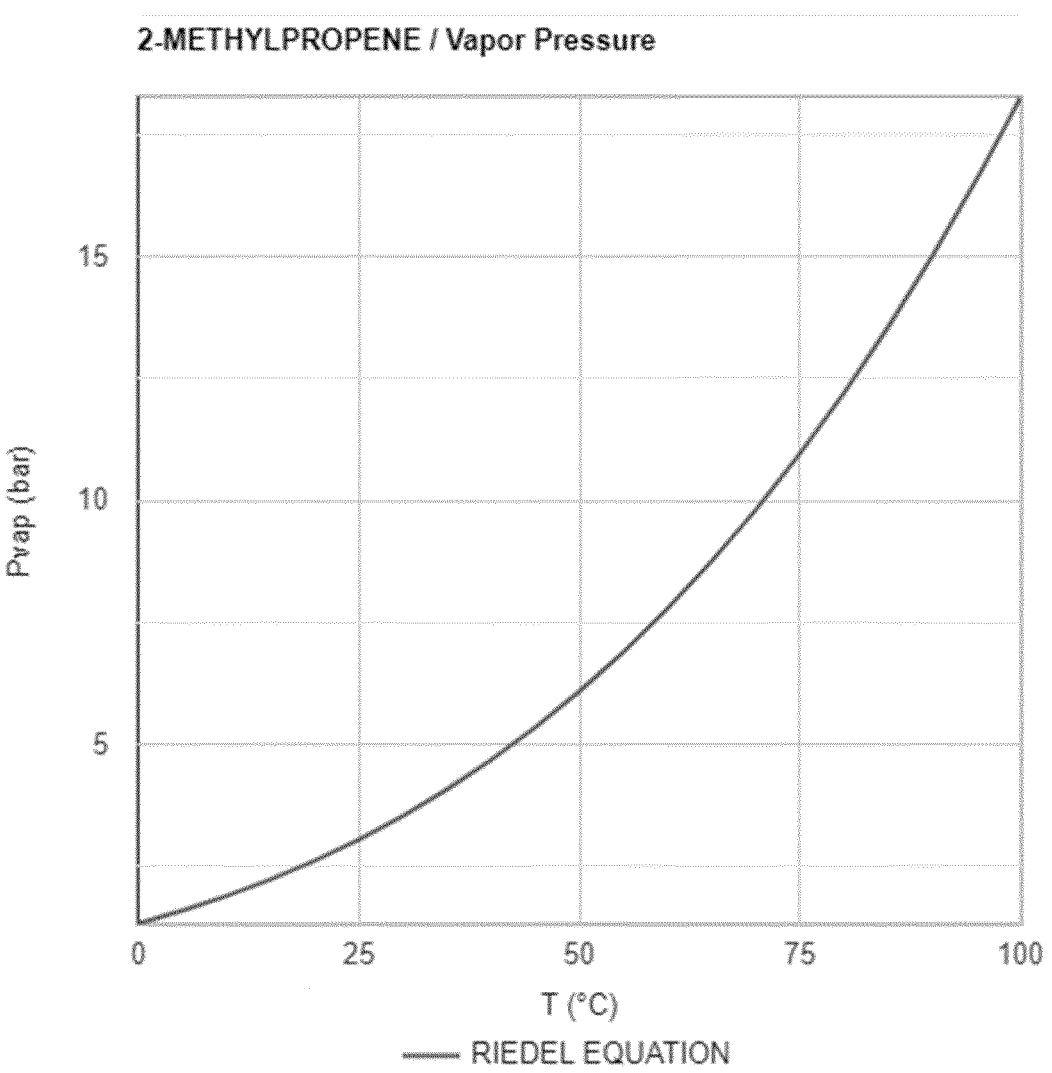

The incubation step (b) of the method according to the present invention is carried out under conditions which allow the isobutene to be in the gaseous state and to evaporate out of the solution. In FIG. 9, a graph is shown which indicates for pure isobutene the correlation between the vapour pressure and the temperature. Below the curve, isobutene is gaseous whereas isobutene is liquid above the curve.

Thus, at temperatures applied for the enzymatic conversion of 3-methylcrotonic acid into isobutene (normally between 30° C. and 40° C.; generally at around 37° C.) and atmospheric pressure, the produced isobutene is produced in gaseous form. The skilled person is easily in a position to select suitable conditions (in terms of adjusting the temperature and/or the pressure in the vessel) in order to have the produced isobutene in its gaseous state of matter.

The produced isobutene which evaporates into the gaseous phase is then recovered according to step (c) of the method according to the present invention. The recovery involves the recovery of the gas which evaporates from the solution and which contains isobutene. The isobutene may subsequently be further purified according to methods well-known to the person skilled in the art.

As described above, the incubation step (b) of the method according to the present invention involves the incubation of the liquid culture medium containing the 3-methylcrotonic acid with an enzyme which can convert the 3-methylcrotonic acid into isobutene or with a microorganism which expresses such an enzyme.

After the stopping of the culturing according to step (a), the transition to step (b) may be effected in different manners. For example, the culture medium resulting at the end of step (a) can be taken as it is (containing the accumulated 3-methylcrotonic acid and the cells of the microorganism used for its production) and can be combined with the enzyme and/or microorganism used in the incubation step (b). In this situation no separation of the cells used in step (a) from the culture medium is effected. The incubation step (b) can be carried out in the same vessel as the cultivation of step (a) by simply adding the enzyme and/or microorganism required for step (b). In a preferred embodiment, the incubation step (b) can be carried out in the same vessel as the cultivation of step (a) by simply adding the enzyme and/or microorganism required for step (b) and by applying optimal conditions for the incubation, i.e., the enzymatic conversion of step (b) by controlling the temperature, pH, agitation forces and/or oxygen concentration by applying corresponding routine measures known in the art. However, it is preferred that the culture medium obtained after stopping the cultivation of step (a) is transferred to a different vessel.

In another embodiment, the method of the present invention comprises a step wherein the liquid culture medium obtained after stopping the culturing of step (a) and containing the 3-methylcrotonic acid is separated from the microorganism prior to step (b). Methods to separate microorganisms from a liquid culture medium are known to the skilled person. As an example, centrifugation may be used for separating the microorganisms from the liquid. Once separated, the liquid culture medium containing said 3-methylcrotonic acid can be subjected to the incubation step (b) of the method of the present invention.

As outlined above, in a second aspect, the present invention provides a method for the production of isobutene from a carbon source characterized in that it comprises:

(a) culturing a microorganism capable of producing 3-methylcrotonic acid from a carbon source in a liquid culture medium, thereby producing said 3-methylcrotonic acid so that it accumulates in the liquid culture medium; and (b) thermochemically converting said 3-methylcrotonic acid contained in the liquid culture medium obtained in step (a) into isobutene, preferably at a temperature between 180° C. and 400° C.; and (c) recovering the produced isobutene.

In step (b), the 3-methylcrotonic acid contained in the liquid culture medium obtained in step (a) is thermochemically converted into isobutene. Preferably, said thermochemical conversion is effected at a temperature between 180° C. and 400° C. The 3-methylcrotonic acid can be efficiently converted into isobutene and carbon dioxide according to procedures known in the art. Preferably, 3-methylcrotonic acid is heated at temperatures between 180° C. and 400° C., preferably between 230° C. to 350° C. In another preferred embodiment, the thermochemical conversion is effected in a boiling reactor, a stirred tank reactor or a tubular reactor. In another preferred embodiment, the thermochemical conversion is effected at a pressure between 0 and 30 bar, preferably between 10 and 30 bar.

In a preferred embodiment, the method of the present invention comprises a step wherein 3-methylcrotonic acid as produced in step (a) of the method of the present invention is isolated or purified from the liquid culture medium prior to step (b) of the method of the present invention. Methods to isolate, purify, extract or separate 3-methylcrotonic acid from the liquid culture medium are known in the art. 3-methylcrotonic acid can, e.g., be concentrated (e.g., by the removal of water content from the liquid culture medium), or (partially) purified, preferably, by the removal of potentially remaining sugars and other compounds that may be present. In addition thereto or in the alternative, 3-methylcrotonic acid can be enriched and/or purified by applying methods known in the art to a concentration of at least 100 g/l more preferable of at least 150 g/l, even more preferable of at least 200 g/l and even more preferable of at least 250 g/l of 3-methylcrotonic acid. Preferably, the 3-methylcrotonic acid is recovered in the form of its sodium or potassium salt.

In another preferred embodiment, the method of the present invention comprises a step wherein 3-methylcrotonic acid as produced in step (a) of the method of the present invention is purified from the liquid culture medium prior to step (b) of the method of the present invention.

In a corresponding preferred embodiment, 3-methylcrotonic acid as produced in step (a) of the method of the present invention can be purified/separated from the liquid culture medium prior to step (b) of the method of the present invention using a batch or a continuous liquid-liquid extraction.

A liquid-liquid extraction of 3-methylcrotonic acid can be performed as follows: Bacteria and all other solids are preferentially removed from the fermentation broth, i.e., from liquid culture medium in terms of the present invention by standard liquid-solid separation. Standard liquid-solid separation may preferably be centrifugation or filtration. Subsequently, the separated fermentation broth, i.e., the separated liquid culture medium can be acidified. Preferably, the acidification is at a pH below 4.2, preferably below 4.0 and more preferably by the addition of any mineral acid. The thus acidified fermentation broth, i.e., the liquid culture medium in terms of the present invention can be mixed with an organic solvent, preferably an alcohol (more preferentially, 2-octanol or 2-ethyl hexanol), a heavy organic acid (more preferentially heptanoic acid), a ketone (more preferentially methyl isobutyl ketone or methyl ethyl ketone), a heavy alkane (more preferentially containing 8, 9, 10, 11, 12, 13, 14, 15, or 16 carbons or mixtures thereof). This mixing can either be made in series of stirred tank reactors or in a continuous liquid-liquid extraction column of any technology known in the art (e.g., by concomitant agitation or without agitation). The organic phase can be recovered and sent to distillation. The solvent can be recovered in the distillate and 3-methylcrotonic acid can be recovered in the residue. Alternatively, the 3-methylcrotonic acid can also further be distillated to be recovered in the distillate.

In another preferred embodiment, the above-described liquid-liquid extraction of 3-methylcrotonic acid can also be performed directly from the liquid culture medium obtained in the culturing of step (a) of the present invention that contains said the 3-methylcrotonic acid and that still the microorganism cultured in step (a).

This can preferably be performed in the culture vessel or fermenter.

In a preferred embodiment, a solvent, preferentially a heavy alkane (containing 8, 9, 10, 11, 12, 13, 14, 15, or 16 carbons or mixtures thereof) can be sent to the culture or fermenter at the beginning of the culture or fermentation or during the culture or fermentation. The resulting mixture can continuously be drawn out from the culture or fermenter. The pH can preferably be acidified reduced down to less than 4.2 to enhance migration of 3-methylcrotonic acid to the solvent. Both phases may be sent to a decanter. The split organic phase is sent to distillation, and aqueous phase still containing the microorganisms can be sent back to the culture or fermenter.

In another preferred embodiment, the above purification/extraction can also take place outside from the culture or fermenter. In such an embodiment, the culture or fermentation takes place in a standard manner, and the broth (i.e., the liquid culture medium of step (a) in terms of the present invention) can continuously be drawn out from the culture or the fermenter. This stream (i.e., the liquid culture medium of step (a) in terms of the present invention which is continuously drawn out from the culture or the fermenter) is preferentially acidified with any mineral acid known in the art, preferably at a pH lower than 4.2. Alternatively, can also not be acidified. The stream (i.e., the liquid culture medium of step (a) in terms of the present invention which is continuously drawn out from the culture or the fermenter) can be mixed with a solvent (preferentially the same heavy alkane) either in a series of stirred tanks, or in a liquid-liquid extraction column as described above. The organic phase is recovered and sent to distillation to recover 3-methylcrotonic acid on one hand, and the solvent on the other hand.

Preferably, in the above-described liquid-liquid extractions, a bio-sourced solvent is used, more preferably, isododecane or 2-octanol.

In the method of the present invention, in the incubation step (b)(i) wherein a microorganism expressing an FMN-dependent decarboxylase associated with an FMN prenyl transferase is incubated with the liquid culture medium containing 3-methylcrotonic acid obtained in step (a) of the present invention, said microorganism can be present as suspension culture (in terms of freely floating around) in the liquid culture medium. Alternatively, the microorganism can be immobilized. The immobilization can be on a suitable carrier, surface and/or support material. Suitable carrier, surface and/or support materials as well as methods of immobilization are known to the skilled person. Martins et al. reviews corresponding support materials as well as methods of immobilization (African Journal of Biotechnology 12(28):441-4418 (2013)).

In the method of the present invention, in the incubation step (b)(ii) wherein an FMN-dependent decarboxylase associated with an FMN prenyl transferase is incubated with said liquid culture medium containing 3-methylcrotonic acid obtained in step (a), said enzyme(s) can be present in solution (in terms of freely floating around) in the liquid culture medium. Alternatively, said enzyme(s) can be immobilized. The immobilization can be on a suitable carrier, surface and/or support material. Suitable carrier, surface and/or support materials as well as methods of immobilization of enzymes are known to the skilled person (see, e.g., Mohamad et al., Biotechnology & Biotechnological Equipment 29(2), 2015, 205-220).

The incubation step (b) is carried out under conditions which allow the conversion of the 3-methylcrotonic acid contained in the solution into isobutene. These conditions depend on the type of organism or enzyme used for the conversion and can be adapted by the skilled person by routine measures.

The incubation is carried out for a time sufficient to allow the production of isobutene. It is possible to monitor during the incubation the concentration of the 3-methylcrotonic acid in the solution. Preferably, the incubation is carried out until at least 90%, more preferably at least 95%, even more preferably at least 98% of the 3-methylcrotonic acid is converted into isobutene.

After the incubation is stopped, the solution may be separated from the cells/enzymes and re-introduced into step (a) of the method. Preferably, the solution is sterilized prior to being re-introduced into step (a) of the method. The cells or enzymes used in step (b) can be recycled and used in another round of step (b).

In a preferred embodiment, in the culturing step (a) of the present invention utilizing a microorganism capable of producing 3-methylcrotonic acid from a carbon source, a microorganism is used which is capable of metabolizing said carbon source into acetyl-CoA prior to its enzymatic conversion into 3-methylcrotonic acid. Corresponding enzymatic conversions and microorganisms, preferably recombinant microorganisms, capable of metabolizing a carbon source into acetyl-CoA and its further enzymatic conversion into 3-methylcrotonic acid are described in more detail further below. However, the method of the present invention is not limited to the use of a corresponding microorganism capable of metabolizing said carbon source into acetyl-CoA prior to its enzymatic conversion into 3-methylcrotonic acid. As explained in more detail further below, there are (recombinant) microorganisms capable of producing 3-methylcrotonic acid from a carbon source wherein the metabolism in these microorganisms does not require the formation of acetyl-CoA as an intermediate.

It is also conceivable, in the culturing step (a) of the present invention using a microorganism capable of producing 3-methylcrotonic acid from a carbon source, to use a C1-fixing microorganism or a combination of microorganisms, preferably of C1-fixing microorganisms.

C1-fixing microorganisms are known in the art and are, e.g., described in WO 2020/188033, the content of which is hereby incorporated by reference.

In a preferred embodiment, the microorganism, preferably the C1-fixing microorganism as defined above, is a microorganism which is capable of consuming more than one sugar. Preferably, said more than one sugar comprises glucose, fructose, sucrose, xylose, glycerol, starch, ethanol, lactic acid, acetic acid and/or mannose. In a more preferred embodiment, the microorganism, preferably the C1-fixing microorganism is a microorganism which is capable of consuming two or more sugars selected from the group consisting of glucose, fructose, sucrose, xylose, glycerol, starch, ethanol, lactic acid, acetic acid and mannose. Organisms and/or microorganisms which are capable of consuming glucose, fructose, sucrose, xylose, glycerol, starch, ethanol, lactic acid, acetic acid and/or mannose do naturally occur and are known in the art.

In a preferred embodiment, the microorganism, preferably the C1-fixing microorganism is an organism which is capable of consuming CO and/or syngas. In another preferred embodiment, the microorganism, preferably the C1-fixing microorganism is an organism which is capable of consuming a mixture of CO and/or $CO_2$ as well as $H_2$.

In another embodiment, said microorganism is genetically modified in order to be capable of consuming glucose, fructose, sucrose, xylose, glycerol, starch, ethanol, lactic acid, acetic acid, mannose and/or CO (or syngas) and/or genetically modified in order to increase the microorganism's capability of consuming glucose, fructose, sucrose, xylose, glycerol, starch, ethanol, lactic acid, acetic acid, mannose and/or CO (or syngas). Corresponding genetic modifications are known in the art.

In another preferred embodiment, the microorganism preferably the C1-fixing microorganism is a microorganism which is capable of consuming sugar through a Phosphotransferase Transport System (PTS).

In a preferred embodiment, the microorganism, preferably the C1-fixing microorganism is an organism which is capable of consuming sugar through a non-Phosphotransferase Transport System (non-PTS).

In a preferred embodiment, in the culturing step (a) of the present invention utilizing a microorganism capable of producing 3-methylcrotonic acid from a carbon source, said carbon source is selected from the group consisting of glucose, fructose, sucrose, xylose, glycerol, starch, ethanol, lactic acid, acetic acid and a mixture thereof.

In a preferred embodiment, in the culturing step (a) of the present invention, the employed microorganism is a recombinant microorganism. Corresponding recombinant microorganisms are described in more detail further below.

In a preferred embodiment, in the culturing step (a) of the present invention, the employed microorganism is a microorganism, preferably a recombinant microorganism, which has a reduced/diminished expression and/or activity of an FMN-dependent decarboxylase associated with an FMN prenyl transferase or which does not express an FMN-dependent decarboxylase associated with an FMN prenyl transferase when said (recombinant) microorganism is cultured according to step (a).

Figure 3:
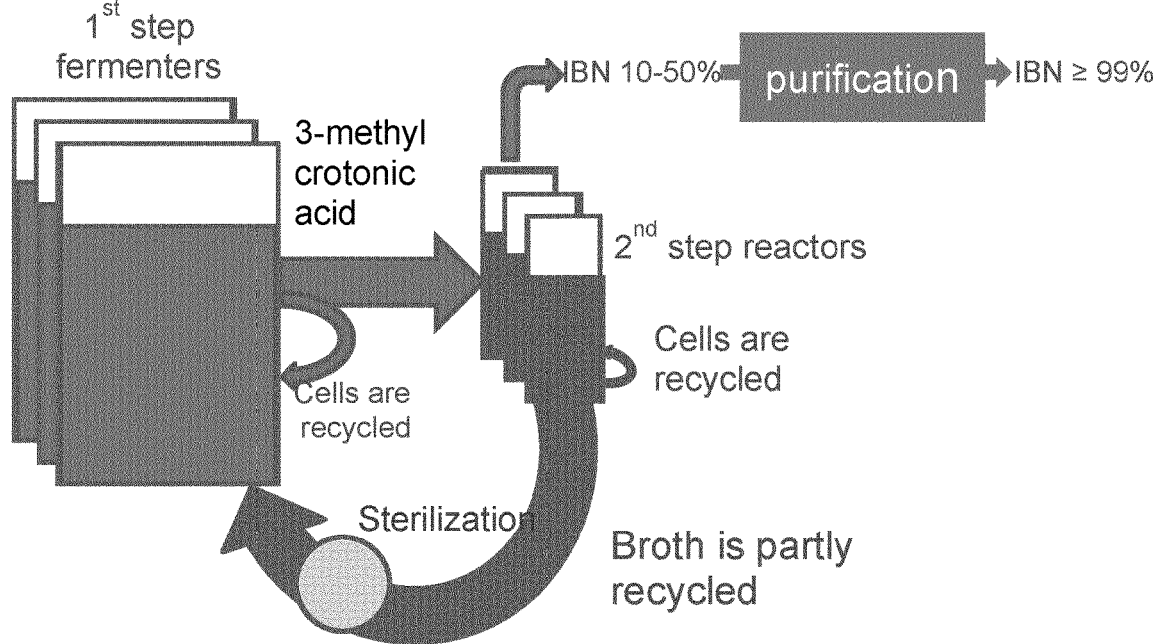

As outlined above, in a preferred embodiment, the method of the present invention comprises a step wherein the liquid culture medium containing said 3-methylcrotonic acid of step (a) is separated from the microorganism prior to step (b). The thus separated microorganism does not necessarily have to be discarded. In fact, in a preferred embodiment, said microorganism separated from the liquid culture medium can be recycled and re-introduced into step (a) of the method of the present invention. A corresponding recycling is schematically illustrated in FIG. 3.

In another preferred embodiment, the microorganism used in step (b)(i) is pre-cultured in a suitable liquid culture medium under suitable conditions prior to the conversion step (b)(i) of the method of the present invention. Without being bound to theory, a corresponding pre-culture step has the effect that the microorganisms are proliferated and enriched to a certain degree which increases the number and/or density of microorganisms (and, correspondingly, of the desired enzymes for the desired enzymatic conversion). Suitable liquid culture media and suitable conditions are known to the skilled person and are described in more detail further below.

The microorganism used in step (b)(i) is preferably added to the solution containing the 3-methylcrotonic acid so as to achieve a cell density, expressed in dry cell weight per liter, of at least 1 g/l, even more preferably of at least 5 g/l and most preferably of at least 10 g/l. As outlined above, the incubation step (b)(i) is preferably carried out under conditions which do not support further proliferation of the cells. Preferably, said incubation step (b)(i) is carried out under conditions which do not support further proliferation of the cells so that the cell density is basically kept constant or only shows a minor increase (preferably not more than 20%, even more preferably not more than 10%) during the incubation. In another preferred embodiment, said incubation step (b)(i) is carried out under conditions which do not support further proliferation of the cells so that the cell density is basically kept constant or only shows a minor decrease (preferably not more than 20%, even more preferably not more than 10%) during the incubation. A decrease of the cell density may occur, e.g., upon lysing of (parts of) the cells, increasing the volume of the liquid culture medium during the incubation by, e.g., adding (acidic) solution(s) when adjusting the pH of the liquid culture medium.

A decrease of the cell density may also occur, e.g., by the addition of 3-methylcrotonic acid to the vessel upon feeding 3-methylcrotonic acid into the vessel during the incubation step (b) as described herein above and below, thereby diluting the biomass/the cells in the solution.

As outlined above, the method of the present invention comprises a step wherein in an incubation step (b), a microorganism expressing an FMN-dependent decarboxylase associated with an FMN prenyl transferase is incubated with said liquid culture medium containing 3-methylcrotonic acid obtained in step (a) of the method of the present invention. Alternatively, the method of the present invention comprises a step wherein in an incubation step (b), an FMN-dependent decarboxylase associated with an FMN prenyl transferase is incubated with said liquid culture medium containing 3-methylcrotonic acid obtained in step (a) of the method of the present invention. In a preferred embodiment, in both cases, after completion of said step (b) of the method of the present invention, said liquid culture medium can be recovered, optionally sterilized and can be re-introduced into step (a) of the method of the present invention. A corresponding recycling is schematically illustrated in FIG. 3.

In another preferred embodiment of the foregoing, microorganisms which are present in the described recovered liquid culture medium (i.e., microorganisms which express an FMN-dependent decarboxylase associated with an FMN prenyl transferase) are removed from said liquid culture medium and re-introduced into the bioconversion step (b)(i) of the method of the present invention. A corresponding recycling is schematically illustrated in FIG. 3.

In another preferred embodiment, the recovered isobutene is subsequently purified and/or enriched.

Purifying or partially purifying in terms of the present invention, preferably, means the (partial or full) removal of potentially remaining other compounds (components other than isobutene) that may be present.

Enriching in terms of the present invention means the increasing of the concentration of isobutene in a gas or liquid phase.

Methods for purifying and/or enriching isobutene are known in the art. Isobutene can be recovered or isolated from the off-gas of the incubation step (b) of the method of the present invention using techniques known in the art, such as, e.g., physical absorption, reactive absorption, adsorption, condensation, cryogenic technologies, and/or membrane-based separation.

In a preferred embodiment, the microorganism(s), preferably the recombinant microorganism(s), used in step (a) and/or step (b) of the method of the present invention is a bacterium, a yeast, a fungus or an algae. In a particularly preferred embodiment, the microorganism is a bacterium, e.g., *E. coli*. Corresponding suitable microorganisms, preferably recombinant microorganisms, are described in more detail further below.

The Enzymatic Production of 3-methylcrotonic Acid from a Carbon Source According to Step (a)

As mentioned above, methods for the enzymatic production of 3-methylcrotonic acid from a carbon source are known in the art and (recombinant) organisms and microorganisms capable of catalyzing the respective enzymatic conversions have been described; see, e.g., WO 2017/085167, WO 2018/206262 and WO 2020/188033, the content of which is hereby incorporated by reference.

Only as examples, without being limited thereto, possible individual steps of enzymatic conversions starting from a carbon source which gives rise to the central metabolite acetyl-CoA and its further conversion into 3-methylcrotonic acid are described.

Acetyl-CoA (acetyl coenzyme A) is a central metabolite present in all organisms and participates in many biochemical reactions in protein, carbohydrate and lipid metabolism. Acetyl-CoA is produced upon, e.g., acetylation of CoA to acetyl-CoA by the breakdown of a carbon source through glycolysis and the breakdown of fatty acids through β-oxidation.

Accordingly, as acetyl-CoA produced from fatty acids, and, in particular, from a carbon source, is a central metabolite present in all organisms, its production is not described herein.

In the following, without being limited thereto, possible individual steps of enzymatic conversions of acetyl-CoA into 3-methylcrotonic acid as well as microorganisms capable of producing 3-methylcrotonic acid, e.g., from acetyl-CoA are summarized. Corresponding enzymatic conversions and microorganisms have been described in, e.g., WO 2017/085167, WO 2018/206262 and WO 2020/188033, the content of which is hereby incorporated by reference.

Figure 2:
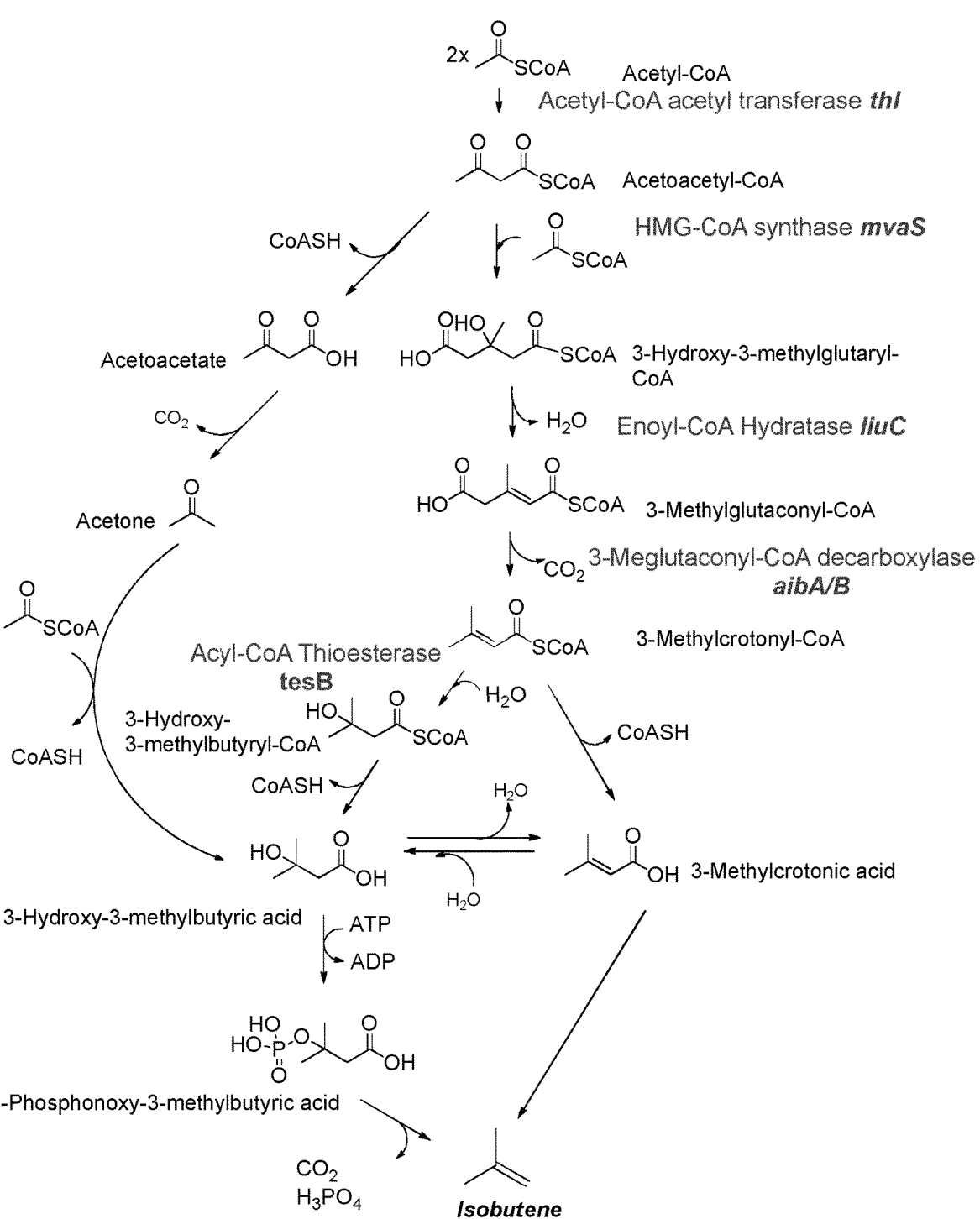

Methods for the production of 3-methylcrotonic acid via different possible routes have been described (see FIG. 1 as well as FIG. 2 for an overview). Methods as well as recombinant organisms and microorganisms utilizing these pathways and enzymatic conversions have, in particular, been described in WO2010/001078, WO2012/052427, WO 2017/085167, WO 2018/206262 and WO 2020/188033 (hereby incorporated by reference).

However, in step (a) of the method of the present invention, not only these reactions can be employed but in principle any other route for the conversion of acetyl-CoA into 3-methylcrotonic acid as described in the prior art documents WO 2017/085167, WO 2018/206262, WO2010/001078, WO2012/052427 and WO 2016/042012.

Moreover, in step (a) of the method of the present invention, said 3-methylcrotonic acid can also be produced as a thioester, namely as 3-methylcrotonyl-CoA from a carbon source or a nitrogen source via pyruvate and leucine. A corresponding biosynthetic pathway as well as microorganisms capable of producing 3-methylcrotonyl-CoA are described in Li et al. (Angew. Chem. Int. Ed. (2013) 52:1304); see, in particular, FIG. 1.

The produced thioester of 3-methylcrotonic acid, i.e., 3-methylcrotonyl-CoA, can then be further converted into 3-methylcrotonic acid by an enzymatic conversion as described in the prior art.

The disclosure of these documents, in particular with respect to preferred embodiments of the enzymes for the individual conversions of the pathways described therein, is herewith incorporated by reference in its entirety. Accordingly, in preferred embodiments, it is preferable to use the enzymes selected from the preferred embodiments described in these prior art documents in connection with the respective enzymatic conversion. Thus, the same applies to the enzymatic conversions of step (a) of the method of the present invention as has been set forth in WO 2017/085167, WO 2018/206262, WO2010/001078, WO2012/052427, WO 2016/042012 and Li et al. (Angew. Chem. Int. Ed. (2013) 52:1304), respectively.

In a preferred embodiment, in step (a) of the method of the present invention, said 3-methylcrotonic acid is produced by the route starting from acetyl-CoA which is subsequently enzymatically converted into acetoacetyl-CoA which is subsequently enzymatically converted into 3-hydroxy-3-methylglutaryl-CoA which is subsequently enzymatically converted into 3-methylglutaconyl-CoA which is subsequently enzymatically converted into 3-methylcrotonyl-CoA which is subsequently enzymatically converted into said 3-methylcrotonic acid (see, e.g., FIG. 2 for an overview). Corresponding methods, enzymatic conversions as well as recombinant organisms and microorganisms utilizing these pathways and enzymatic conversions have been described in the above-cited prior art documents. The disclosure of these documents, in particular with respect to preferred embodiments of the enzymes for the above preferred pathway (i.e., the conversions starting from acetyl-CoA via acetoacetyl-CoA then via 3-hydroxy-3-methylglutaryl-CoA then via 3-methylglutaconyl-CoA then via 3-methylcrotonyl-CoA and then into said 3-methylcrotonic acid), is herewith incorporated by reference in its entirety. Accordingly, in preferred embodiments regarding this possible preferred pathway, it is preferable to use the enzymes selected from the preferred embodiments described in these prior art documents in connection with the respective enzymatic conversion. Thus, the same applies to the enzymatic conversions of step (a) of the method of the present invention as has been set forth in the above prior art documents.

As mentioned above, in a preferred embodiment, in the culturing step (a) of the present invention, said microorganism used in step (a) is a microorganism, preferably, a recombinant microorganism, which has a reduced/diminished activity of an FMN-dependent decarboxylase associated with an FMN prenyl transferase (preferably an FMN-dependent decarboxylase capable of enzymatically converting 3-methylcrotonic acid into isobutene). Using a corresponding microorganism which has a reduced/diminished activity of an FMN-dependent decarboxylase associated with an FMN prenyl transferase (preferably an FMN-dependent decarboxylase capable of enzymatically converting 3-methylcrotonic acid into isobutene) is beneficial as it avoids the metabolization of the thus produced 3-methylcrotonic acid and, accordingly, allows the accumulation of 3-methylcrotonic acid in said liquid culture medium.

Accordingly, the microorganism which has a reduced/diminished activity of an FMN-dependent decarboxylase associated with an FMN prenyl transferase (preferably an FMN-dependent decarboxylase capable of enzymatically converting 3-methylcrotonic acid into isobutene) is either a microorganism which naturally does not express an FMN-dependent decarboxylase associated with an FMN prenyl transferase or a microorganism which has been modified, in particular genetically modified, so that the respective enzymes' activity/activities is/are either completely abolished or so that the activity/activities is/are reduced/diminished compared to the corresponding non-modified microorganism.

Corresponding microorganisms which naturally do not express an FMN-dependent decarboxylase associated with an FMN prenyl transferase (preferably an FMN-dependent decarboxylase capable of enzymatically converting 3-methylcrotonic acid into isobutene) are known in the art.

In a preferred embodiment, the microorganisms having a reduced/diminished activity of an FMN-dependent decarboxylase associated with an FMN prenyl transferase (preferably an FMN-dependent decarboxylase capable of enzymatically converting 3-methylcrotonic acid into isobutene) as compared to a non-modified organism or microorganism preferably refers to a microorganism in which the reduction/diminishing of the respective enzymatic activity/activities as compared to a non-modified microorganism is achieved by a genetic modification of the microorganism which leads to said inactivation or reduction.

In a preferred embodiment, the recombinant microorganism of the present invention is a recombinant microorganism that has a reduced/diminished FMN-dependent decarboxylase associated with an FMN prenyl transferase (preferably an FMN-dependent decarboxylase capable of enzymatically converting 3-methylcrotonic acid into isobutene) by reducing the activity of a FMN-dependent decarboxylase associated with an FMN prenyl transferase as compared to a non-modified microorganism. Preferably, this reduction is achieved by a genetic modification of the microorganism.

This can be achieved e.g., by random mutagenesis or site-directed mutagenesis of the promoter and/or the enzyme and subsequent selection of promoters and/or enzymes having the desired properties or by complementary nucleotide sequences or RNAi effect as described above.

In the context of the present invention, a "reduced activity" means that the activity of an enzyme, in particular of the FMN-dependent decarboxylase associated with an FMN prenyl transferase, in the genetically modified microorganism is at least 10%, preferably at least 20%, more preferably at least 30% or 50%, even more preferably at least 70% or 80% and particularly preferred at least 90% or 100% lower than in the corresponding non-modified microorganism. Assays for measuring the reduced enzyme activity of a FMN-dependent decarboxylase associated with an FMN prenyl transferase are known in the art.

In another embodiment the microorganism according to the present invention is a microorganism which does not possess an activity of a FMN-dependent decarboxylase associated with an FMN prenyl transferase (preferably an FMN-dependent decarboxylase capable of enzymatically converting 3-methylcrotonic acid into isobutene). This preferably means that such a microorganism naturally does not possess an activity of a FMN-dependent decarboxylase associated with an FMN prenyl transferase. This means that such a microorganism does naturally not contain in its genome a nucleotide sequence encoding an enzyme with an activity of an FMN-dependent decarboxylase associated with an FMN prenyl transferase.

In another preferred embodiment, the microorganism of the present invention is an organism which is genetically modified in order to avoid the leakage of acetyl-CoA, thereby increasing the intracellular concentration of acetyl-CoA, which finally converted into 3-methylcrotonic acid. Genetic modifications leading to an increase in the intracellular concentration of acetyl-CoA are known in the art. Such a microorganism may preferably be genetically modified by deleting or inactivating the following genes: ΔackA (acetate kinase), Aldh (lactate dehydrogenase), ΔadhE (alcohol dehydrogenase), ΔfrdB and/or ΔfrdC (fumarate reductase and fumarate dehydrogenase).

In preferred embodiments, methods are utilized wherein the yield, pool and/or flux of acetyl-CoA is increased. Corresponding methods as well as recombinant organisms and microorganisms having an increased pool of acetyl-CoA are described in the prior art, e.g., in WO2013/007786, WO2020/021051 and WO2020/188033, the content of which is hereby incorporated by reference.

In preferred embodiments, the yield, pool and/or flux of acetyl-CoA is increased by utilizing a recombinant organism or microorganism having a phosphoketolase (PKT) activity as described in, e.g., WO2013/007786, WO2020/021051 and WO2020/188033, the content of which is hereby incorporated by reference.

The Enzymatic Conversion of 3-methylcrotonic Acid into Isobutene According to Step (b)

As outlined above, in the incubation step (b)(i) or (b)(ii) of the method of the present invention, an FMN-dependent decarboxylase associated with an FMN prenyl transferase or a microorganism expressing such an enzyme is used and is incubated with the liquid culture medium containing 3-methylcrotonic acid obtained in step (a) of the present invention.

In principle, any FMN-dependent decarboxylase associated with an FMN prenyl transferase (or a microorganism which expresses it) can be employed in step (b) of the method according to the present invention. The use of such enzymes for the conversion of 3-methylcrotonic acid into isobutene has been described in the prior art, e.g., in WO 2017/085167, WO 2018/206262 and WO 2020/188033 (hereby incorporated by reference).

In the following, the enzymatic conversion of 3-methylcrotonic acid into isobutene is described using an FMN-dependent decarboxylase associated with an FMN prenyl transferase capable of the enzymatic conversion of 3-methylcrotonic acid into isobutene. Whenever reference is made to an FMN-dependent decarboxylase associated with an FMN prenyl transferase in terms of the present invention, reference can also more precisely be made to "a prenylated FMN-dependent decarboxylase" and for ease of reference.

The enzymatic conversion of 3-methylcrotonic acid into isobutene is schematically shown in step I of FIG. 1). This conversion can be achieved by a decarboxylation by making use of an FMN-dependent decarboxylase associated with an FMN prenyl transferase. "Decarboxylation" is generally a chemical reaction that removes a carboxyl group and releases carbon dioxide ($CO_2$).

The enzymatic conversion of 3-methylcrotonic acid into isobutene utilizing an FMN-dependent decarboxylase associated with an FMN prenyl transferase relies on a reaction of two consecutive steps catalyzed by the two enzymes, i.e., the FMN-dependent decarboxylase (catalyzing the actual decarboxylation of 3-methylcrotonic acid into isobutene) with an associated FMN prenyl transferase which provides the modified flavin cofactor.

The flavin cofactor may preferably be FMN or FAD. FMN (flavin mononucleotide; also termed riboflavin-5'-phosphate) is a biomolecule produced from riboflavin (vitamin B2) by the enzyme riboflavin kinase and functions as prosthetic group of various reactions. FAD (flavin adenine dinucleotide) is a redox cofactor, more specifically a prosthetic group, involved in several important reactions in metabolism.

Thus, in the conversion of 3-methylcrotonic acid into isobutene, in a first step, a flavin cofactor (FMN or FAD) is modified into a (modified) flavin-derived cofactor. This modification is catalyzed by said FMN prenyl transferase. FMN prenyl transferase prenylates the flavin ring of the flavin cofactor (FMN or FAD) into a (modified) prenylated flavin cofactor. More specifically, FMN prenyl transferase catalyzes the prenylation of a flavin cofactor (FMN or FAD) utilizing dimethylallyl phosphate (DMAP) or dimethylallyl pyrophosphate (DMAPP) into a flavin-derived cofactor.

In a second step, the actual conversion of 3-methylcrotonic acid into isobutene is catalyzed by said FMN-dependent decarboxylase via a 1,3-dipolar cycloaddition based mechanism wherein said FMN-dependent decarboxylase uses the prenylated flavin cofactor (FMN or FAD) provided by the associated FMN prenyl transferase.

In a preferred embodiment, said FMN prenyl transferase which modifies the flavin cofactor (FMN or FAD) into a (modified) flavin-derived cofactor (utilizing dimethylallyl phosphate (DMAP) or dimethylallyl pyrophosphate (DMAPP)) is a phenylacrylic acid decarboxylase (PAD)-type protein, or the closely related prokaryotic enzyme UbiX, an enzyme which is involved in ubiquinone biosynthesis in prokaryotes.

In Escherichia coli, the protein UbiX (also termed 3-octaprenyl-4-hydroxybenzoate carboxy-lyase) has been shown to be involved in the third step of ubiquinone biosynthesis.

In a preferred embodiment, the modification of a flavin cofactor (FMN or FAD) into the corresponding (modified) flavin-derived cofactor is catalyzed by the FMN-containing protein phenylacrylic acid decarboxylase (PAD). The enzymes involved in the modification of the flavin cofactor (FMN or FAD) into the corresponding modified flavin-derived cofactor were initially annotated as decarboxylases (EC 4.1.1.-). Some phenylacrylic acid decarboxylases (PAD) are now annotated as flavin prenyl transferases as EC 2.5.1.-. Enzymes capable of catalyzing the enzymatic reaction described herein for flavin prenyl transferases have recently also been annotated as flavin prenyl transferases as EC 2.5.1.129.

In a more preferred embodiment, the conversion of 3-methylcrotonic acid into isobutene makes use of a phenylacrylic acid decarboxylase (PAD)-type protein as the FMN prenyl transferase which modifies a flavin cofactor (FMN or FAD) into the corresponding (modified) flavin-derived cofactor wherein said phenylacrylic acid decarboxylase (PAD)-type protein is derived from Candida albicans (Uniprot accession number Q5A8L8), Aspergillus niger (Uniprot accession number A3F715), Saccharomyces cerevisiae (Uniprot accession number P33751) or Cryptococcus gattii (Uniprot accession number E6R9Z0).

In another preferred embodiment, the modification of a flavin cofactor (FMN or FAD) into the corresponding (modified) flavin-derived cofactor is catalyzed by the FMN-containing protein 3-octaprenyl-4-hydroxybenzoate carboxy-lyase also termed UbiX (initially annotated EC 4.1.1.-). As mentioned above, the enzymes involved in the modification of the flavin cofactor (FMN or FAD) into the corresponding modified flavin-derived cofactor were initially annotated as decarboxylases. Some phenylacrylic acid decarboxylases (PAD) are now annotated as flavin prenyl transferases as EC 2.5.1.-. As mentioned above, enzymes capable of catalyzing the enzymatic reaction described herein for flavin prenyl transferases have recently also been annotated as flavin prenyl transferases as EC 2.5.1.129.

In a more preferred embodiment, the conversion of 3-methylcrotonic acid into isobutene makes use of a 3-octaprenyl-4-hydroxybenzoate carboxy-lyase (also termed UbiX) as the FMN prenyl transferase which modifies the flavin cofactor (FMN or FAD) into the corresponding (modified) flavin-derived cofactor wherein said 3-octaprenyl-4-hydroxybenzoate carboxy-lyase (also termed UbiX) is derived from Escherichia coli (Uniprot accession number POAG03), Bacillus subtilis (Uniprot accession, number A0A086WXG4), Pseudomonas aeruginosa (Uniprot accession number A0A072ZCW8) or Enterobacter sp. DC4 (Uniprot accession number W7P6B1).

In another preferred embodiment, the modification of a flavin cofactor (FMN or FAD) into the corresponding (modified) flavin-derived cofactor is catalyzed by an Ubx-like flavin prenyl transferase derived from E. coli encoded by kpdB and ecdB, respectively (UniProt accession number A0A023LDW3 and UniProt accession number P69772, respectively), and an UbiX-like flavin prenyl transferase derived from Klebsiella pneumoniae encoded by kpdB (UniProt accession number Q462H$_4$).

In another preferred embodiment, the modification of a flavin cofactor (FMN or FAD) into the corresponding (modified) flavin-derived cofactor is catalyzed by a flavin prenyl transferase.

As mentioned above, the actual decarboxylation, i.e., the conversion of 3-methylcrotonic acid into isobutene is catalyzed by an FMN-dependent decarboxylase via a 1,3-dipolar cycloaddition based mechanism wherein said FMN-dependent decarboxylase uses the prenylated flavin cofactor (FMN or FAD) provided by any of the above described associated FMN prenyl transferases.

In a preferred embodiment, said FMN-dependent decarboxylase catalyzing the decarboxylation of 3-methylcrotonic acid into isobutene is catalyzed by a ferulic acid decarboxylase (FDC). Ferulic acid decarboxylases (FDC) belong to the enzyme class EC 4.1.1.-.

In an even more preferred embodiment, the conversion of 3-methylcrotonic acid into isobutene makes use of a ferulic acid decarboxylases (FDC) which is derived from Saccharomyces cerevisiae (Uniprot accession number 003034), Enterobacter sp. (Uniprot accession number V3P7U0),

*Bacillus pumilus* (Uniprot accession number Q45361), *Aspergillus niger* (Uniprot accession number A2ROP7) or *Candida* dubliniensis (Uniprot accession number B9WJ66).

In another more preferred embodiment, the conversion of 3-methylcrotonic acid into isobutene makes use of a protocatechuate decarboxylase (EC 4.1.1.63).

In a preferred embodiment of the present invention, the PCA decarboxylase employed in the method of the present invention is a PCA decarboxylase which is derived from *Klebsiella pneumoniae* (Uniprot accession number B9AM6), Leptolyngbya sp. (Uniprot accession number A0A0S3U6D8), or Phascolarctobacterium sp. (Uniprot accession number R6∥V6).

In another preferred embodiment, said FMN-dependent decarboxylase catalyzing the decarboxylation of 3-methylcrotonic acid into isobutene is an enzyme which is closely related to the above ferulic acid decarboxylase (FDC), namely a 3-polyprenyl-4-hydroxybenzoate decarboxylase (also termed UbiD). 3-polyprenyl-4-hydroxybenzoate decarboxylase belongs to the UbiD decarboxylase family classified as EC 4.1.1.-.

In a more preferred embodiment, the conversion of 3-methylcrotonic acid into isobutene makes use of a 3-polyprenyl-4-hydroxybenzoate decarboxylase (UbiD) which is derived from Hypocrea atroviridis (UniProt Accession number G9NLP8), *Sphaerulina musiva* (UniProt Accession number M3DF95), *Penecillinum requeforti* (UniProt Accession number W6QKP7), *Fusarium oxysporum f.* sp. *lycopersici* (UniProt Accession number W9LTH3), *Saccharomyces kudriavzevii* (UniProt Accession number J8TRN5), *Saccaromyces cerevisiae, Aspergillus parasiticus, Candida albicans, Grosmannia clavigera, Escherichia coli* (Uniprot accession number P0AAB4), *Bacillus megaterium* (Uniprot accession number D5DTL4), Methanothermobacter sp. CaT2 (Uniprot accession number T2GKK5), *Mycobacterium chelonae* 1518 (Uniprot accession number X8EX86) or *Enterobacter cloacae* (Uniprot accessin number V3DX94).

In another more preferred embodiment, the conversion of 3-methylcrotonic acid into isobutene makes use of an UbiD-like decarboxylase which is derived from *Streptomyces* sp (UniProt Accession number A0A0A8EV26).

In a preferred embodiment, in the incubation step (b)(i) of the method of the present invention, a microorganism expressing an FMN-dependent decarboxylase associated with an FMN prenyl transferase is used which overexpresses such (an) enzyme(s) and/or which expresses such (an) enzyme(s) which show improved properties, such as a higher enzyme activity or a higher substrate specificity.

In another preferred embodiment, in the incubation step (b)(ii) of the method of the present invention, an FMN-dependent decarboxylase associated with an FMN prenyl transferase is used which has been produced with a microorganism overexpressing such (an) enzyme(s) and/or (an) enzyme(s) is/are used which show improved properties, such as a higher enzyme activity or a higher substrate specificity. Corresponding recombinant microorganisms and enzyme(s) which show such improved properties have been described in the prior art, e.g., in WO2018/206262. The disclosure of this document, in particular with respect to the overexpression of such (an) enzyme(s) and/or (an) enzyme(s) which show improved properties, such as a higher enzyme activity or a higher substrate, is herewith incorporated by reference in its entirety.

The present invention also contemplates alternative ways of producing isobutene from 3-methylcrotonic acid or from compounds closely related to 3-methylcrotonic acid. For example, in one embodiment, it is also conceivable that the culturing step (a) of the above-described method according to the present invention is omitted and 3-methylcrotonic acid (regardless of how it has been produced) is used in an incubation step (b) as described above in which the gas-supply is controlled so as to allow an efficient conversion of 3-methylcrotonic acid into isobutene.

Accordingly, in one embodiment, the present invention relates to a method in terms of the present invention wherein the culturing step (a) is omitted and 3-methylcrotonic acid is (directly) fed into the vessel used in incubation step (b). Thus, in one embodiment, the present invention relates to a method for the production of isobutene from 3-methylcrotonic acid characterized in that it comprises:

(a) feeding 3-methylcrotonic acid into a liquid medium in a vessel; and (b) enzymatically converting said 3-methylcrotonic acid contained in the liquid medium into isobutene by:
  (i) incubating a microorganism expressing an FMN-dependent decarboxylase associated with an FMN prenyl transferase with said liquid culture medium containing 3-methylcrotonic acid obtained in step (a); and/or
  (ii) incubating an FMN-dependent decarboxylase associated with an FMN prenyl transferase with said liquid culture medium containing 3-methylcrotonic acid obtained in step (a);
  thereby producing said isobutene; and (c) recovering the produced isobutene,
wherein said incubation of step (b) is carried out in
  (a) said vessel without gas supply; or
  (b) said vessel with gas supply at <0.1 vvm (vessel volume per minute) using an inlet gas.

The term "feeding 3-methylcrotonic acid into a liquid medium in a vessel" means that 3-methylcrotonic acid is provided to a liquid medium in the vessel in which the incubation step (b) should be carried out. This can be achieved by first providing a liquid medium in which the incubation should be carried out in the vessel and then adding the 3-methylcrotonic acid to said medium at the desired concentration or by providing a medium which already contains 3-methylcrotonic acid in the vessel. The microorganism/enzyme used for achieving the conversion of 3-methylcrotonic acid can be added before providing the 3-methylcrotonic acid, after providing the 3-methylcrotonic acid or simultaneously. Moreover, during the incubation step (b) 3 methylcrotonic acid can be fed into the medium in the vessel. This can be done continuously or in batches. In this manner, it is, e.g. possible to maintain the concentration of 3-methylcrotonic acid in the medium at a desired level which allows an efficient conversion into isobutene. Thus, in such an embodiment it is also envisaged that the concentration of 3-methylcrotonic acid in the medium is monitored (e.g. constantly or at pre-determined time intervals) and the concentration is adjusted to a desired concentration by feeding additional 3-methylcrotonic acid into the medium. As regards further preferred embodiments for the incubation step (b), the same applies as has been set forth above in connection with the first aspect of the present invention.

In another alternative, the present invention also relates to the method as described above in which, however, in step (a) not 3-methylcrotonic acid is produced but rather a hydrated form of 3-methylcrotonic acid (i.e., 3-hydroxy-3-methylbutyric acid (also known as 3-hydoxyisovaleric acid, HIV)).

Methods for the production of 3-hydroxy-3-methylbutyric acid via different possible routes have been described (see FIG. 2 for an overview). Methods as well as recombinant organisms and microorganisms utilizing these pathways and enzymatic conversions have, e.g., been described in WO2012/052427, WO 2017/085167 and WO 2016/042012.

The disclosure of these documents, in particular with respect to preferred embodiments of the enzymes for the individual conversions of the pathways described therein leading to 3-hydroxy-3-methylbutyric acid, is herewith incorporated by reference in its entirety. Accordingly, in preferred embodiments, it is preferable to use the enzymes selected from the preferred embodiments described in these prior art documents in connection with the respective enzymatic conversions. In such an alternative method, once 3-hydroxy-3-methylbutyric acid is produced in step (a), the incubation step (b) then comprises the production of 3-methylcrotonic acid from the thus produced 3-hydroxy-3-methylbutyric acid, preferably by a thermochemical conversion, by dehydrating it into 3-methylcrotonic acid (see FIG. 2 for an illustration). In the same step (b), the thus produced 3-methylcrotonic acid is then converted into isobutene as described above.

In another preferred embodiment, as outlined above for the thermochemical conversion of 3-methylcrotonic acid contained in the liquid culture medium obtained in step (a) into isobutene, mutatis mutandis, in the above alternative wherein 3-hydroxy-3-methylbutyric acid instead of 3-methylcrotonic acid, said 3-hydroxy-3-methylbutyric acid contained in the liquid culture medium obtained in step (a) is thermochemically converted into isobutene, preferably at a temperature between 180° C. and 400° C. Thus, in a corresponding step (b), the 3-hydroxy-3-methylbutyric acid contained in the liquid culture medium obtained in step (a) is thermochemically converted into isobutene. Preferably, said thermochemical conversion is effected at a temperature between 180° C. and 400° C.

The 3-hydroxy-3-methylbutyric acid can be efficiently converted into isobutene and carbon dioxide according to procedures known in the art. Preferably, 3-hydroxy-3-methylbutyric acid is heated at temperatures between 180° C. and 400° C., preferably between 230° C. to 350° C. In another preferred embodiment, the thermochemical conversion is effected in a boiling reactor, a stirred tank reactor or a tubular reactor. In another preferred embodiment, the thermochemical conversion is effected at a pressure between 0 and 30 bar, preferably between 10 and 30 bar.

Preferably, 3-hydroxy-3-methylbutyric acid is converted into isobutene, water and carbon dioxide which are in a gaseous form.

In another alternative embodiment, the present invention relates to the method as described above in which, however, in step (a), not 3-methylcrotonic acid is produced but rather a phosphorylated form of 3-hydroxy-3-methylbutyric acid (i.e., 3-phosphonoxy-3-methylbutyric acid; also known as 3-phosphonoxyisovaleric acid (PIV)).

Methods for the production of 3-phosphonoxy-3-methylbutyric acid via different possible routes have been described (see FIG. 2 for an overview). Methods as well as recombinant organisms and microorganisms utilizing these pathways and enzymatic conversions have, e.g., been described in WO2012/052427, WO 2017/085167 and WO 2016/042012.

The disclosure of these documents, in particular with respect to preferred embodiments of the enzymes for the individual conversions of the pathways described therein leading to 3-phosphonoxy-3-methylbutyric acid, is herewith incorporated by reference in its entirety. Accordingly, in preferred embodiments, it is preferable to use the enzymes selected from the preferred embodiments described in these prior art documents in connection with the respective enzymatic conversions.

In such an alternative method, once 3-phosphonoxy-3-methylbutyric acid is produced in step (a), the incubation step (b) then comprises the production of 3-hydroxy-3-methylbutyric acid from the thus produced 3-phosphonoxy-3-methylbutyric acid, preferably by a dephosphorylation of 3-phosphonoxy-3-methylbutyric acid (wherein hydrolysis leads to the formation of an —OH bond) (see FIG. 2 for an illustration) wherein step (b) then further comprises the production of 3-methylcrotonic acid from the thus produced 3-hydroxy-3-methylbutyric acid, preferably by a thermochemical conversion, by dehydrating it into 3-methylcrotonic acid.

In the same step (b), the thus produced 3-methylcrotonic acid is then converted into isobutene as described above.

Alternatively, in such an alternative method, once 3-phosphonoxy-3-methylbutyric acid is produced in step (a), the incubation step (b) then comprises the direct production 3-methylcrotonic acid from the thus produced 3-phosphonoxy-3-methylbutyric acid, preferably by a dephosphorylation and a concomitant double bond formation.

In the same step (b), the thus produced 3-methylcrotonic acid is then converted into isobutene as described above.

In a further alternative embodiment, the present invention relates to the method as described above in which, however, in step (a), not 3-methylcrotonic acid is produced but rather a hydrated form of 3-methylcrotonic acid (i.e., 3-hydroxy-3-methylbutyric acid (also known as 3-hydoxyisovaleric acid, HIV)) and a phosphorylated form of 3-hydroxy-3-methylbutyric acid (i.e., 3-phosphonoxy-3-methylbutyric acid; also known as 3-phosphonoxyisovaleric acid (PIV)) as described above.

In such an alternative method, once 3-hydroxy-3-methylbutyric acid is produced in step (a), the incubation step (b) then comprises the production of 3-methylcrotonic acid from the thus produced 3-hydroxy-3-methylbutyric acid as described above. In the same step (b), the thus produced 3-methylcrotonic acid is then converted into isobutene as described above.

Moreover, in such an alternative method, once 3-phosphonoxy-3-methylbutyric acid is produced in step (a), the incubation step (b) then comprises the production of 3-hydroxy-3-methylbutyric acid from the thus produced 3-phosphonoxy-3-methylbutyric acid and further the production of 3-methylcrotonic acid as described above and/or the direct production of 3-methylcrotonic acid from the thus produced 3-phosphonoxy-3-methylbutyric acid as described above. In the same step (b), the thus produced 3-methylcrotonic acid is then converted into isobutene as described above.

As mentioned above, the method according to the present invention is in particular useful for large scale production of isobutene in vivo, in particular for a commercial production. The present invention describes novel means and ways to commercially and cost-effectively produce large quantities of isobutene which has not been obtainable to date. The generated large quantities of isobutene can then be further converted, in a commercial setting, to produce large quantities of, e.g., drop-in gasoline (e.g. isooctane, ETBE, MTBE), jet-fuel, cosmetics, chemicals, such as methacrylic acid, polyisobutene, or butyl rubber. As used herein, "large scale production", "commercial production" and "bioprocessing" of isobutene in a fermentation vessel or in vitro is carried out at a capacity greater than at least 100 liters, and preferably greater than at least 400 liters, or more preferably production of 1,000 liters of scale or more, even more preferably production of 5,000 liters of scale or more. As used herein, "large quantities" specifically excludes trace amounts that may be produced inherently in an microorganism.

FIG. 1: shows artificial pathways for isobutene production from acetyl-CoA via 3-methylcrotonic acid. Moreover, enzymatic recycling of metabolites which may occur during the pathway are shown in steps Xa, Xb, XI and XII.

FIG. 2: shows the main routes of artificial pathway for isobutene production from acetyl-CoA via 3-methylcrotonyl-CoA and a possible route from 3-methylcrotonyl-CoA via 3-methylcrotonic acid into isobutene while for certain steps, the corresponding enzymes are indicated.

FIG. 3: shows a process diagram of a large scale plant. IBN: isobutene.

Figure 4:
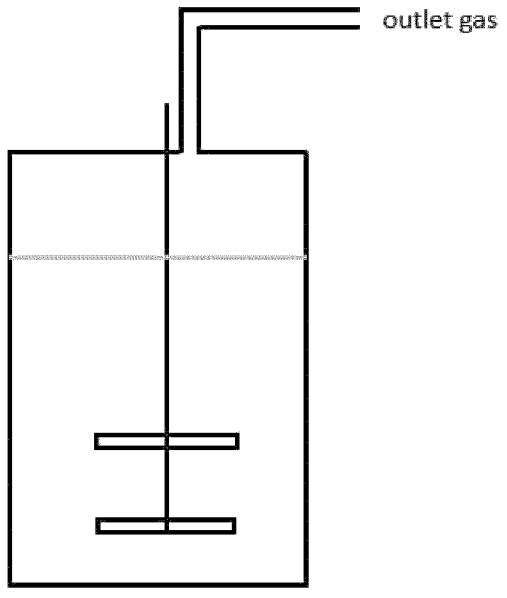
Figure 4:
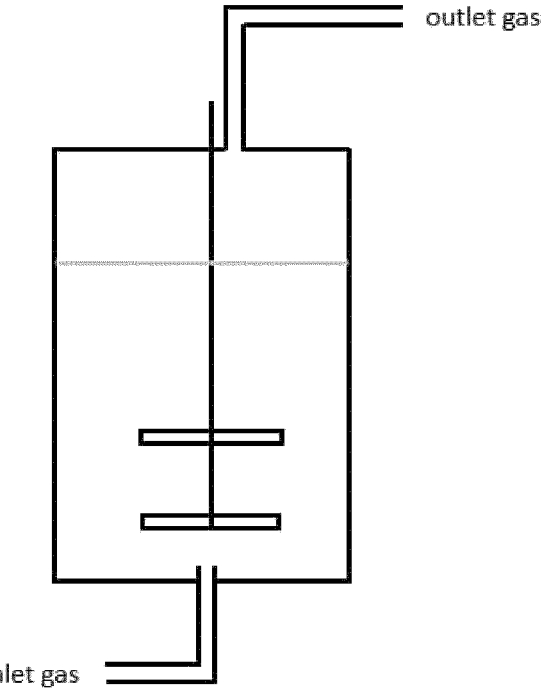

FIG. 4: schematically illustrates a vessel for the incubation "without gas supplying" (upper Figure) and "with gas supplying at <0.1 vvm (vessel volume per minute) using an inlet gas" (lower Figure), respectively.

Figure 5:
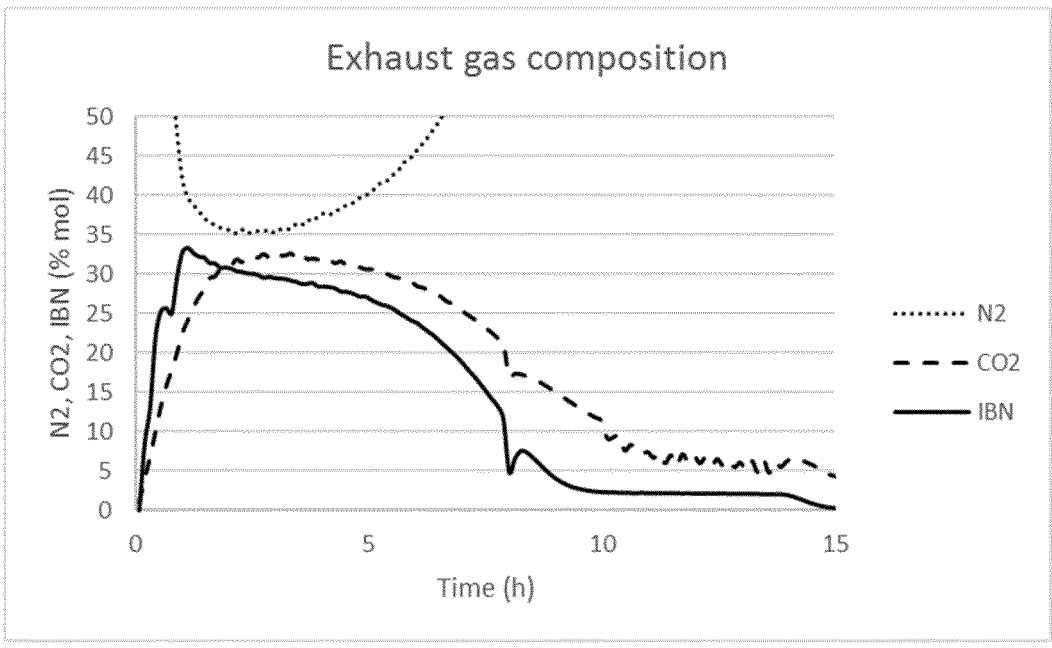

FIG. 5: shows the composition of the exhaust gas over time regarding $N_2$, $CO_2$ and isobutene (IBN).

Figure 6:
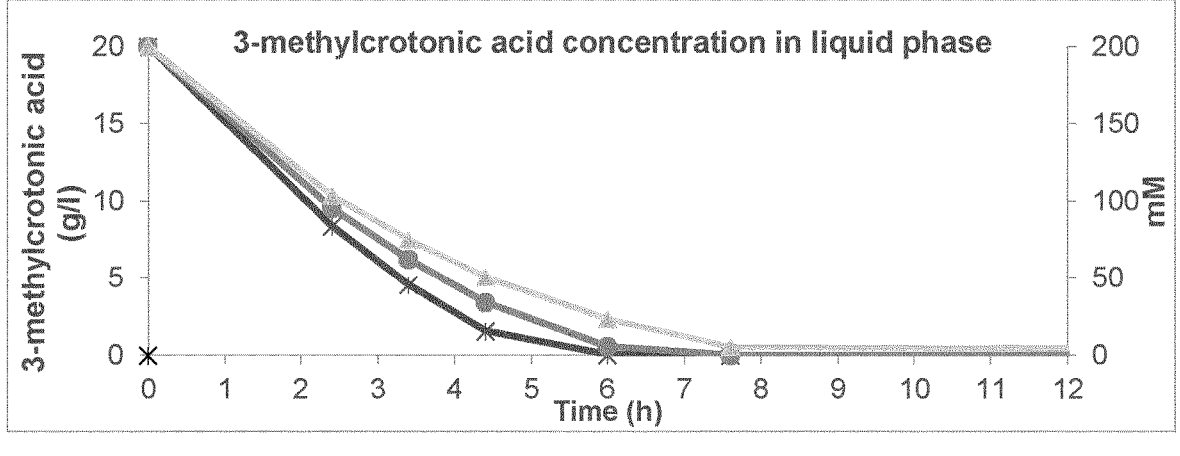

FIG. 6: shows the isobutene (IBN) and 3-methylcrotonic acid consumption rate.

Figure 7:
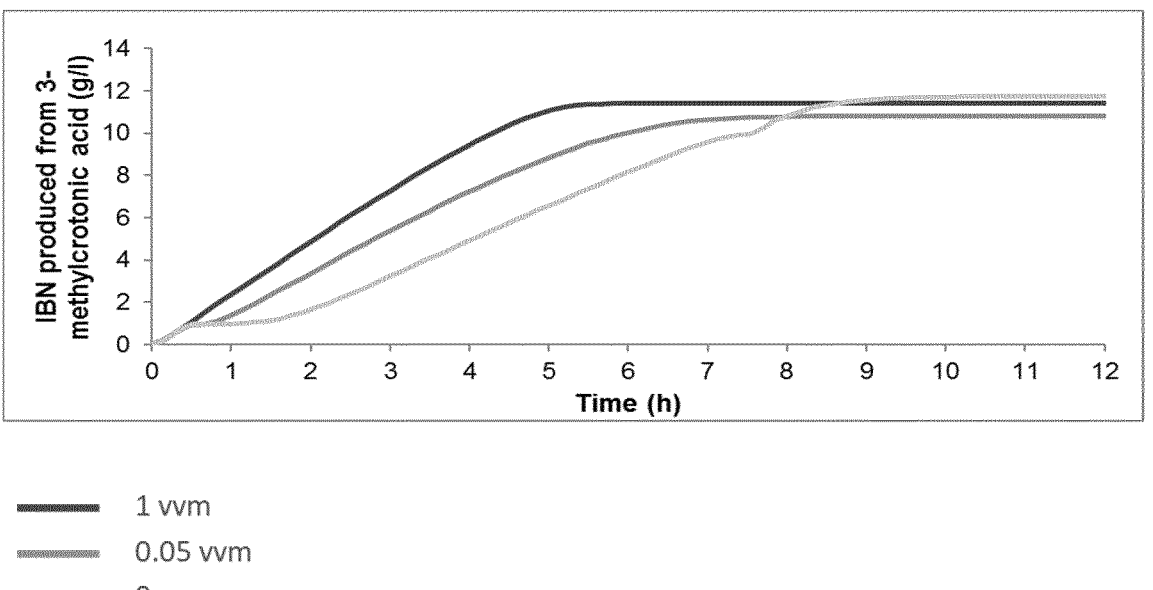

FIG. 7: shows the IBN total production and that 100% of 3-methylcrotonic acid is converted into isobutene (IBN).

Figure 8:
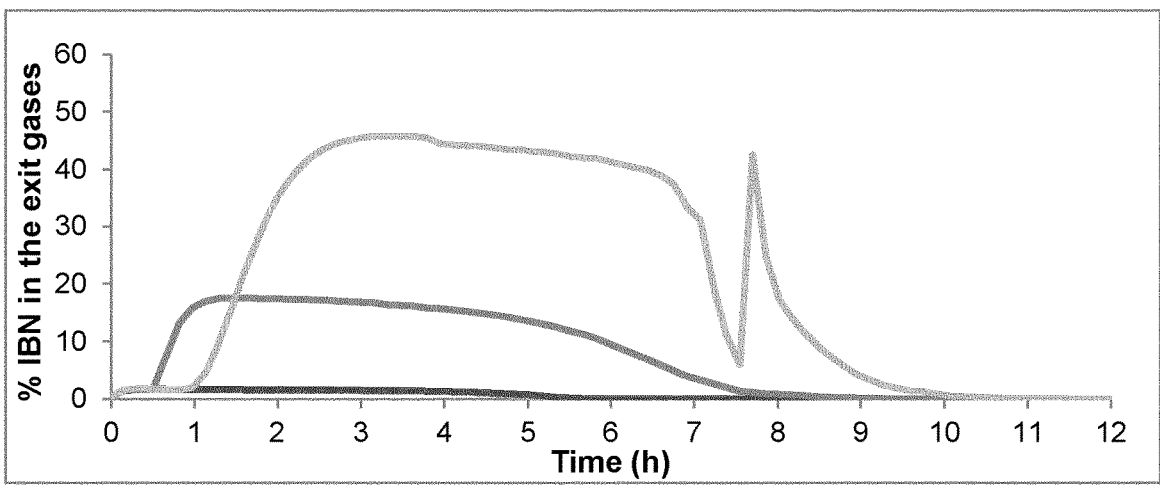
Figure 8:
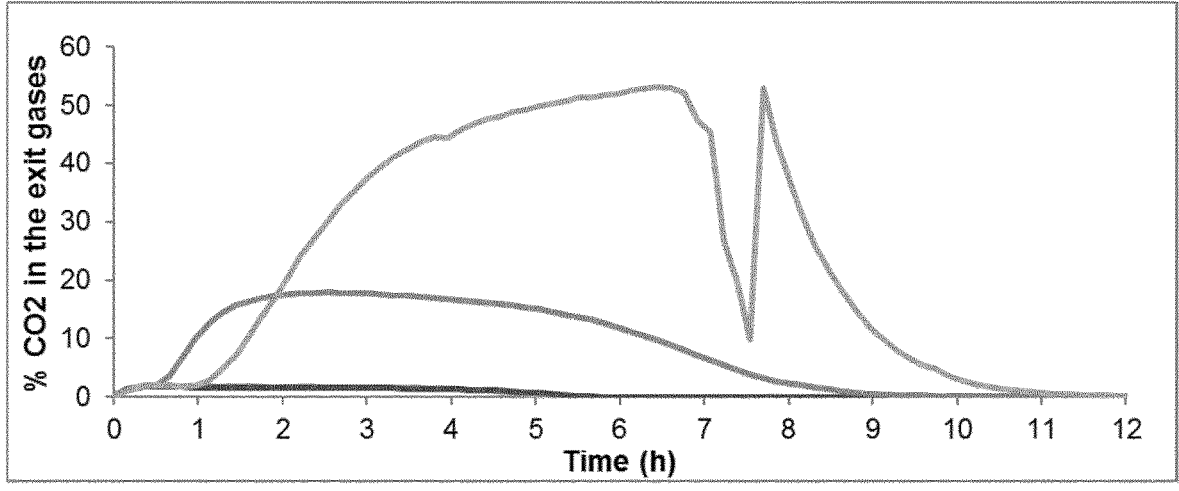

FIG. 8: shows that high concentrations of IBN and $CO_2$ is produced during an incubation without gas supplying and with gas supplying at <0.1 vvm (vessel volume per minute), respectively, vs. an incubation with gas supplying at 1 vvm.

FIG. 9: shows a correlation between temperature and pressure at which isobutene is gaseous in a vessel. Above the curve, isobutene is liquid.

Below the curve isobutene is gaseous.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLES

Example 1: Isobutene Production by a Two-Step Process in a 15 L Reactor

First step: In vivo 3-methylcrotonic acid production from acetyl-CoA This Example shows the production of 3-methylcrotonic acid by a recombinant *E. coli* strain which expresses exogenous genes, thereby constituting the 3-methylcrotonic acid pathway.

Like most microorganisms, *E. coli* converts glucose into acetyl-CoA. The enzymes used in this study to convert acetyl-CoA into 3-methylcrotonic acid (FIG. 2) are summarized in the following.

Expression of a 3-methyicrotonic acid biosynthetic pathway in *E. coli* The following genes were codon-optimized for the expression in *E. coli* and synthesized by GeneArt (Life Technologies):

thl from *Clostridium acetobutylicum* (Uniprot Accession number Q6LD78)

ech (enoyl CoA hydratase) from *Pseudomonas* sp. (Uniprot Accession number K9NHK2)

mvaS from *Schizosaccharomyces pombe* (Uniprot Accession number P54874)

aibA and aibB that code for the 2 subunits of glutaconate CoA transferase from *Myxococcus* hansupus (Uniprot Accession number AKQ65711.1 and AKQ65710.1).

men/from *Escherichia coli* (strain K12) (Uniprot Accession number P77781)

An expression vector containing the origin of replication of pSC101 (reference: http://www.ncbi.nlm.nih.gov/pmc/articles/PMC320470/) was used for the expression of the genes: mvaS, Ech, aibA, aibB, ydil according to the procedure described in WO2017/085167, Example 12, except for the integration of the FDC1 gene. The recombinant pGBE13786 plasmid was verified by sequencing.

The strain MG1655 was modified by integration of the thl gene from *Clostridium acetobutylicum* into the ssrS locus. The resulting strain (GB119077) was made electro-competent and was transformed with pGBE13786.

The transformed cells, strain SB1429, were then plated on LB plates and supplied with tetracyclin. Plates were incubated overnight at 30° C. An isolated colony was used to prepare a pre-culture as described in the following.

Production of 3-Methyl Crotonic Acid

A 15 L vessel was filled with 6 L of a culture medium containing 15 g/L yeast extract, 50 mM sodium glutamate, 4 mM magnesium sulfate, 5 mM sodium sulfate, 10 mM ammonium sulfate, 25 mM potassium dihydrogene phosphate and 25 mM disodium hydrogenephosphate and sterilized at 121° C. for 20 minutes. After cooling, filter sterilized vitamins were added at a final concentration of 0.6 mM for thiamin and 5 mM for calcium panthotenate. Filter sterilized trace metals were also added at a final concentration of 10 μM iron Ill chloride, 4 μM calcium chloride, 2 μM manganese chloride, 2 μM zinc sulfate, 0.4 μM copper chloride and 0.4 μM sodium molybdate. Then filter sterilized glucose was added at a final concentration of 1 g/L.

In addition to the batch culture medium, two fed batch solutions were prepared. The first one was a filter sterilized 300 g/L yeast extract solution. The second one was a 700 g/L glucose solution containing also 5 g/L magnesium sulfate heptahydrate, 10 mM sodium glutamate and trace metals at a final concentration of 50 μM iron Ill chloride, 20 μM calcium chloride, 10 μM manganese chloride, 10 μM zinc sulfate, 2 μM copper chloride and 2 μM sodium molybdate.

The culture medium was inoculated with 500 mL of a pre-culture of strain (SB1429) previously grown in LB medium containing 50 mM sodium glutamate at 30° C. and tetracycline. Temperature was kept at 32° C. for 30 hours and then increased up to 34° C. Aeration was set at 0.77 vvm and agitation was regulated to maintain dissolved oxygen at 5% of saturation.

After 6 h of culture, 400 mL of yeast extract solution were added continuously over a 18 h period of time. In parallel, a glucose fed batch was started 8 h after the start of the culture and the specific feed rate was maintained at 0.1 g glucose per g dry cell weight per hour for 22 h.

Then the specific feed rate was first increased to 0.25 g/g/h and later was adjusted to maintain low levels of glucose and acetate in the culture medium. 3-methylcrotonic acid production was monitored by HPLC and fermentation was stopped when acetic acid started to accumulate instead of the desired product.

More than 20 g/L of 3-methylcrotonic acid were then produced when fermentation was stopped. The culture medium was then clarified by centrifugation and used in the second step as well in the Example 2.

Second Step: Isobutene Production from 3-methylcrotonic Acid pSC101 Derivative Vector (reference: http://www.ncbi.nlm.nih.gov/pmc/articles/PMC320470/) was used to express a mutant of prenylated FMN-dependent 3-methylcrotonic acid decarboxylase (FDC) from *Streptomyces* sp 769 (UniProt Accession number A0A0A8EV26) and Ubx-like flavin prenyl transferase derived from *Klebsiella pneumoniae* (kpdB; UniProt accession number Q462H$_4$). *E. coli* MG1655 cells was transformed with the constructed plasmid and the cells of the newly obtained strain SB1505 were grown to a cell density of about 35 g/L on a rich medium containing yeast extract and mineral salts with glucose as a carbon source. Cells were collected by centrifugation and resuspended in the supernatant at a concentration of 250 g/L and kept at 4° C. for up to 3 weeks before use.

A 15 L reactor was filled with 12 L of a culture medium containing 3-methylcrotonate and agitated at 800 RPM. The temperature was set at 37° C. and pH regulated at 6.3 with phosphoric acid 20%. The vessel was ventilated with nitrogen through a sparger to flush the air from the headspace of the reactor (about 3 L) and pressure was regulated at 0.5 bar. Outlet gas was analyzed and when oxygen was no longer detected the gas supply nitrogen was set at 0.017 vvm. 1 L of concentrated cells of the strain MB 106 was added in the vessel to start the production of isobutene.

At that time, the concentration of 3-methylcrotonic acid was 231 mM.

The composition of exhaust gas over the time is shown in FIG. 5.

The production of isobutene was stopped when 3-methylcrotonic acid was no longer detected in the culture medium.

Example 2: Production of Isobutene from 3-Methycrotonic Acid in a 1 L Reactor The incubation step was carried out in a 1 L vessel under the following conditions:

| Parameters | Values |
|---|---|
| Concentration of cells (MB106) | 11 g/L |
| Temperature | 37° C. |
| pH | 6.5 |
| Stirring | 1000 rpm |
| Nature of inlet gas | N$_2$ |
| Inlet flow rate | 1 vvm until O$_2$ concentration in the exit gases was under 0.1%, then either 1 vvm or 0.05 vvm or 0 vvm (for this vessel, after 7.5 hours of incubation, inlet flow rate was adjusted to 0.05 vvm until the end of the experiment) |

The incubation media was compose of:

| Products | Final Concentrations |
|---|---|
| Sodium sulfate (Na$_2$SO$_4$) | 0.71 g/L |
| Ammonium sulfate ((NH$_4$)$_2$SO$_4$) | 1.3375 g/L |
| Potassium phosphate monobasic (KH$_2$PO$_4$) | 3.4 g/L |

-continued

| Products | Final Concentrations |
|---|---|
| Sodium phosphate dibasic (Na$_2$HPO$_4$) | 4.45 g/L |
| 3-methylcrotonic acid (see Example 1) | 20 g/L |

The outlet gas (IBN, CO$_2$) as well as 3-methylcrotonic acid consumption were monitored over time.

The results are shown in FIG. 6 (showing the isobutene (IBN) and 3-methylcrotonic acid consumption rate), FIG. 7 (showing the IBN total production and that 100% of 3-methylcrotonic acid is converted into isobutene (IBN)) and FIG. 8 (showing that high concentrations of IBN and CO$_2$ are produced during an incubation without gas supplying and with gas supplying at <0.1 vvm, respectively, vs. an incubation with gas supplying at 1 vvm).

Summary:

It has been shown that, when gas supplying is low (0.05 vvm) or without any gas supplying (0 vvm):

IBN concentrations is high (and, accordingly, easy to purify)

there is no risk of combustion/explosivity.

Example 3: 3-methylcrotonic Acid Purification, Process 1

A 15-liter fermenter was run according to the conditions described in Example 1. The biomass was removed by centrifugation, leading to 10.8 L of supernatant at 29 g/L 3 methylcrotonate. The resulting supernatant was then acidified by the addition of 270 g of 98% sulfuric acid until the pH was adjusted to pH 3.5 prior to the evaporation step.

Evaporation was run using a rotavapor R300, (Buchi) at heating temperature of 80° C., cooling temperature of 10° C. and a pressure of 150 mbar. Crystals of 3-methylcrotonic acid were recovered on the condenser. They were removed by washing with water and mixed with the distillate. Evaporation was run until the residue became viscous. 11.7 kg of distillate containing 24.5 g/L of 3-methylcrotonic acid were recovered.

Then, 600 g of 3M-sodium hydroxide were added to the distillate, in order to adjust the pH at a value of 9.1. Evaporation was run at a heating temperature of 80° C., cooling temperature of 10° C., and at a pressure of 150 mbar until solids appeared in the residue. 900 g of sodium 3-methylcrotonate at 35 w % were recovered.

488 g of 20%-sulfuric acid and 11 g of 80%-sulfuric acid were added, leading to the precipitation of 3-methylcrotonic acid. The slurry was filter on Buchner, leading to 488 g of wet solid at 57 w % 3-methylcrotonic acid.

Example 4: 3-methylcrotonic Acid Purification, Process 2

A 15-liter fermenter was run according to conditions described in Example 1. The biomass was removed by centrifugation, leading to 7.1 L of supernatant at 27.3 g/L 3 methylcrotonate. Then alkalinization was performed by the addition of 204 g of 3M-sodium hydroxide to adjust the pH to pH 9.0.

Evaporation was run using a rotavapor R300, (Buchi) at heating temperature of 80° C., cooling temperature of 10° C. and a pressure of 150 mbar. Evaporation was run until solids appeared in the residue. 1.4 kg of distillate containing 117 g/L of 3-methylcrotonic acid were recovered.

The distillate was cooled down to 10° C. and filtered on Buchner.

Then, 165 g of 98%-sulfuric acid were added to the residue, in order to adjust the pH to 3.78. Evaporation was run at a heating temperature of 80° C., cooling temperature of 10° C., at a pressure of 150 mbar until solids appeared in the residue. 900 g of sodium 3-methylcrotonate at 35 w % were recovered, leading to 146 g of wet solid at 52 w % 3-methylcrotonic acid.

Example 5: 3-methylcrotonic Acid Purification, Process 3

In a 200 mL, glass, jacketed stirred cell, 40 mL of clarified broth (obtained according to Example 1) containing 21 g/L 3-methylcrotonate was introduced. The broth was then acidified to pH=2 by the addition of 98% sulfuric acid. 40 mL of solvent were then added to the cell in a 1/1 vol %/vol % ratio. The following solvents were tested in this experiment:

2-octanol (CAS number: 123-96-6)

Isododecane (IDD, CAS number: 31807-55-3)

Heptanoic acid (CAS number: 111-14-8)

4-Methyl-2-pentanone (CAS number: 108-10-1)

The temperature of the cell was set to 20° C. and the mixture was stirred vigorously for 2 hours. Stirring was then stopped, while two liquid phases were allowed to form during 16 h. Finally, each phase was recovered separately, and weighted.

Each phase was then analyzed as follows:

Aqueous phases were analyzed as follows:

LC-RID: quantification of 3-methylcrotonic acid

Dry mass at 200° C.

Organic phases were analyzed as follows:

Karl Fisher: water quantification

Dry mass at 200° C.

Measured partition coefficients (K) are shown in the following Table:

| Solvents | K (3-methylcrotonic acid) |
|---|---|
| 2-octanol/clarified culture broth | 28.9 |
| IDD/clarified culture broth | 2.6 |
| Heptanoic acid/clarified culture broth | 26.6 |
| MIBK/clarified culture broth | 25.8 |

This demonstrates that the four solvents tested can be efficiently used for a liquid-liquid extraction of the 3-methylcrotonic acid out of the fermentation broth.

3-methylcrotonic acid was extracted from 1 kg of clarified fermentation broth at 2.5 w % 3-methylcrotonic acid, 1.1 w % acetic acid. 1 kg 2-octanol was added and stirred during 16 hours. After decantation, the mass of organic phase was 1.03 kg. The composition was 97.1 w % 2-octanol, 2.3 w % prenic acid, 0.5 w % acetic acid, 0.02 w % water. This mixture was distilled in a batch column of 21 theoretical plates, at a pressure of 100 mbar, and a reflux ratio of 2. First fractions contained 2-octanol, acetic acid and water: their compositions changed over time, until only 2-octanol was recovered on the top of the distillation column. When the temperature increased on the middle of the distillation column (indicating that prenic acid was evaporated, too), the reflux ratio was enhanced up to 5. An intermediate fraction containing 35% 2-octanol and 65% prenic acid was recovered. Next fraction was made of 4.9 g of prenic acid at 99.9%.

Example 6: Thermal Conversion of 3-methylcrotonic Acid into Isobutene 3-methylcrotonic acid as obtained in the above Examples 3 to 5 is melted to a temperature of 70° C. and sent to a stirred tank reactor, tubular reactor). The reactor operates at a temperature of minimum 220° C. and a pressure between 10 and 30 bar. 3-methylcrotonic acid is converted into isobutene and carbon dioxide which are on gaseous form.

Example 7: Thermal Conversion of 3-methylcrotonic Acid into Isobutene 3-methylcrotonic acid is melt at 100° C. and continuously pumped. It is preheated up to 85° C. and sent to a reactor at a flow rate of 22 g/h. The reactor is a tubular one (280 mL—1 inch diameter) containing glass beads of 2 mm. Reactor pressure is 15 bar and temperature is 290° C. After the reactor, two liquid traps (successively made of water and ethanol and water) are added, so that the gas has to go through the liquid. After 115 minutes running, samples are analyzed. Isobutene over $CO_2$ ratio is measured 65 (area ratio on GC) showing 3-methylcrotonic acid to isobutene yield is 95%. Collected liquids in the traps are analyzed by GC-MS show only traces of impurities. Some 3-methylcrotonic acid remains in the reactor, explaining that the conversion rate into isobutene is less 100%.

Example 8: Thermal Conversion of 3-methylcrotonic Acid into Isobutene 3-methylcrotonic acid is melt at 100° C. and continuously pumped. It is preheated up to 85° C. and sent to a reactor at a flow rate of 22 g/h. The reactor is a tubular one (280 mL—1 inch diameter) containing glass beads of 2 mm. Reactor pressure is 25 bar and temperature is 290° C. After the reactor, two liquid traps (successively made of water and ethanol and water) are added, so that the gas has to go through the liquid. After 70 minutes running, samples are analyzed. 3-methylcrotonic acid to isobutene yield is measured 101%. Collected liquids in the traps are analyzed by GC-MS show only traces of impurities. Some 3-methylcrotonic acid is recovered in the reactor.

Example 9: 3-hydroxy-3-methylbutyric Acid Production from Acetyl-CoA

This Example shows the production of 3-hydroxy-3-methylbutyric acid by a recombinant E. coli strain which expresses exogenous genes, thereby constituting the 3-hydroxy-3-methylbutyric acid pathway.

Like most microorganisms, E. coli converts glucose into acetyl-CoA. The enzymes used in this study to convert acetyl-CoA into 3-hydroxy-3-methylbutyric acid (FIG. 2) are summarized in the following.

9.1 Expression of a 3-Hydroxy-3-Methylbutyric Acid Biosynthetic Pathway in E. coli The following genes were codon-optimized for the expression in E. coli and synthesized by GeneArt (Life Technologies):

thl from Clostridium acetobutylicum (Uniprot Accession number P45359)

mvaS from Enterococcus faecalis (Uniprot Accession number P54874)

aibA and aibB that code for the 2 subunits of glutaconate CoA transferase from Myxococcus hansupus (Uniprot Accession number A0A0H4WQB1 and A0A0H4WWJ4).

tesB from *Escherichia coli* (strain K12) (Uniprot Accession number P0AGG2)

liuC from *Myxococcus xanthus* (Uniprot Accession number Q1 D5Y4)

An expression vector containing the origin of replication of pSC101 (reference: http://www.ncbi.nlm.nih.gov/pmc/articles/PMC320470/) was used for the expression of the genes: mvaS, Ech, aibA, aibB, men/, liuC according to the procedure described in WO2017/085167, Example 12, except for the integration of the FDC1 gene on one hand and the substitution of the ech gene by the liuC gene on the other hand. The recombinant pGB 5550 plasmid was verified by sequencing (SEQ ID NO:1).

The strain MG1655 was modified by integration of the thl gene from *Clostridium acetobutylicum* into the ssrS locus.

Deletions of ackA, pta and poxB genes were performed in order to reduce acetyl-CoA conversion to acetate. The gene ldhA was also deleted to reduce lactate production.

The resulting strain (GB119706) was made electro-competent and was transformed with plasmid pGB 5550.

The transformed cells, strain SB1 653, were then plated on LB plates and supplied with spectinomycin. Plates were incubated overnight at 30° C. An isolated colony was used to prepare a pre-culture as described in the following.

9.2 Production of 3-Hydroxy-3-Methylbutyric Acid in Fed Batch Mode

A 1 L vessel was filled with 0.5 L of a culture medium containing 5 g/L yeast extract, 10 g/L tryptone, 50 mM sodium glutamate, 4 mM magnesium sulfate, 5 mM sodium sulfate, 10 mM ammonium sulfate, 25 mM potassium dihydrogen phosphate and 25 mM disodium hydrogen phosphate and sterilized at 121° C. for 20 minutes. After cooling, filter sterilized vitamins were added at a final concentration of 0.6 mM for thiamin and 5 mM for calcium panthotenate, and 50 mg/L of filter sterilized spectinomycin was also introduced in the culture medium. Filter sterilized trace metals were also added at a final concentration of 10 μM iron Ill chloride, 4 μM calcium chloride, 2 μM manganese chloride, 2 μM zinc sulfate, 0.4 μM copper chloride and 0.4 μM sodium molybdate. Then filter sterilized glucose was added at a final concentration of 1 g/L.

In addition to the batch culture medium, two fed batch solutions were prepared. The first one was a filter sterilized 250 g/L yeast extract solution. The second one was a 600 g/L glucose solution containing also 5 g/L magnesium sulfate heptahydrate, 20 g/l sodium glutamate and trace metals at a final concentration of 50 μM iron Ill chloride, 20 μM calcium chloride, 10 μM manganese chloride, 10 μM zinc sulfate, 2 μM copper chloride and 2 μM sodium molybdate.

The culture medium was inoculated with 500 mL of a pre-culture of strain SB1653 previously grown in LB medium containing 50 mM sodium glutamate at 30° C. and 50 mg/L spectinomycin. Temperature was kept at 32° C. for 30 hours and then increased up to 34° C. Aeration was set at 2 vvm and agitation was regulated to maintain dissolved oxygen at 5% of saturation. pH was regulated at 6.5.

After 8 h, 12 h and 16 h of culture, 10 mL of yeast extract solution were added each time. In parallel, a glucose fed batch was started 8 h after the start of the culture and the specific feed rate was maintained at 0.08 g glucose per g dry cell weight per hour for 22 h.

Then the feed rate was increased to deliver 4 g/l/h glucose and later was adjusted to maintain low levels of glucose and acetate in the culture medium. 3-hydroxy-3-methylbutyric acid production was monitored by HPLC and fermentation was stopped when acetic acid started to accumulate instead of the desired product.

More than 80 g/L of 3-hydroxy-3-methylbutyric acid were then produced when fermentation was stopped.

9.3 Production of 3-Hydroxy-3-Methylbutyric Acid in Semi-Continuous Mode

A 1 L vessel was filled with 0.5 L of a culture medium containing 15 g/L yeast extract, 13.4 g/l sodium glutamate, 2.2 g/l magnesium sulfate, 0.85 g/l potassium dihydrogen phosphate and 1.1 g/l disodium hydrogen phosphate and sterilized at 121° C. for 20 minutes. After cooling, filter sterilized vitamins were added at a final concentration of 0.6 mM for thiamin and 5 mM for calcium panthotenate, and 50 mg/L of filter sterilized spectinomycin were also introduced in the culture medium. Filter sterilized trace metals were also added at a final concentration of 10 μM iron Ill chloride, 4 μM calcium chloride, 2 μM manganese chloride, 2 μM zinc sulfate and 0.4 μM copper chloride. Then filter sterilized glucose was added at a final concentration of 5 g/L.

In addition to the batch culture medium, two fed batch solutions were prepared. The first one was a filter sterilized 600 g/L glucose solution. The second one was a saline solution containing 0.85 g/l potassium dihydrogen phosphate, 1.1 g/l disodium hydrogen phosphate, 2 g/L magnesium sulfate heptahydrate, 50 μM iron Ill chloride, 20 μM calcium chloride, 10 μM manganese chloride, 10 μM zinc sulfate and 2 μM copper chloride. The 1 L vessel was connected to a vivaflow 200 PES (200 cm², 0.2 p) module (Sartorius) in order to recycle cells while maintaining the volume of culture at about 0.5 liter and in order to obtain a permeate containing 3-hydroxy-3-methylbutyric acid.

The culture medium was inoculated with 500 mL of a pre-culture of strain (SB1653) previously grown in LB medium containing 50 mM sodium glutamate at 30° C. and spectinomycin. Temperature was kept at 32° C. Aeration was set at 0.5 vvm and agitation was regulated to maintain dissolved oxygen at 5% of saturation. pH was regulated at 7.5 using 30% ammonia solution and 5 M phosphoric acid.

After 7.5 h of culture 5 g/l of glucose were added. Then after 9 h of culture a feed of 3 g/l/h of glucose was applied for 7 hours. After 16 h of culture a specific feed of 0.3 g glucose per g dry cell weight per hour was applied.

3-hydroxy-3-methylbutyric acid production was monitored by HPLC and more than 12 L of 3-hydroxy-3-methylbutyric acid solution were produced when fermentation was stopped.

Example 10: Purification of 3-hydroxy-3-methylbutyric Acid (HMB) by Concentration 590 ml of broth obtained as described in Example 9.2 and containing 48 g 3-hydroxy-3-methylbutyric acid (HMB) were centrifuged. The supernatant was recovered and brought to pH 3.3 with concentrated sulfuric acid. Then the acidified broth was concentrated to 90 ml using a Buchi 300 evaporator at 50° C. and under a pressure of 20 mbar. The concentrate was centrifuged to remove solids and the supernatant was evaporated again in a similar manner to a volume of 35 ml. This new concentrate was also centrifuged and finally 26 ml of homogeneous supernatant were recovered containing 18 g HMB (684 g/L).

Example 11: Purification of 3-hydroxy-3-methylbutyric Acid (HMB) by Liquid Extraction 11.9 L of permeate at pH 7.6 obtained as described in Example 9.3 and containing 177 g 3-hydroxy-3-methylbutyric acid (HMB) and about 153 g acetic acid were concentrated to 1.7 L using a Buchi 300 evaporator at 80° C. and under a pressure of 180 mbar. The concentrate was brought to pH 3.84 with concentrated sulfuric acid and then extracted twice with first 1.3 L and then 1.1 L MIBK (methyl isobutyl ketone). The two MIBK layers were combined and evaporated using a Buchi 300 evaporator at 85° C. and under a pressure of 150 mbar first and down to 10 mbar at the end of the operation. 125 ml of a liquid phase (132 g) were recovered containing 93 g HMB and 10 g acetic acid.

---

The invention claimed is:

1. A method for the production of isobutene from a carbon source characterized in that it comprises:

(a) culturing a microorganism capable of producing 3-methylcrotonic acid from a carbon source in a liquid culture medium, thereby producing said 3-methylcrotonic acid so that it accumulates in the liquid culture medium; and (b) enzymatically converting said 3-methylcrotonic acid contained in the liquid culture medium obtained in step (a) into isobutene by:

(i) incubating a microorganism expressing an FMN-dependent decarboxylase associated with an FMN prenyl transferase with said liquid culture medium containing 3-methylcrotonic acid obtained in step (a); and/or

45

(ii) incubating an FMN-dependent decarboxylase associated with an FMN prenyl transferase with said liquid culture medium containing 3-methylcrotonic acid obtained in step (a);

thereby producing said isobutene; and (c) recovering the produced isobutene.

2. The method of claim 1, wherein said incubation of step (b) is carried out in (a) a vessel without gas supply; or (b) a vessel with gas supply at <0.1 vvm (vessel volume per minute) using an inlet gas.

3. The method of claim 1, wherein the liquid culture medium containing said 3-methylcrotonic acid of step (a) is separated from the microorganism prior to step (b).

4. The method of claim 1, wherein said 3-methylcrotonic acid is isolated or purified from said liquid culture medium prior to step (b) of claim 1.

5. The method of claim 1, wherein said inlet gas is air, inert gas or a mixture of air and inert gas, wherein said inert gas is selected from nitrogen, helium, argon, neon, $CO_2$ and a mixture of these gases.

6. The method of claim 1, wherein said carbon source is metabolized into acetyl-CoA prior to its enzymatic conversion into 3- methylcrotonic acid.

7. The method of claim 6, wherein said carbon source is selected from the group consisting of glucose, fructose, sucrose, xylose, glycerol, starch, ethanol, lactic acid, acetic acid and a mixture thereof.

8. The method of claim 1, wherein said microorganism used in claim 1 (b) (i) is pre-cultured in a suitable liquid culture medium under suitable conditions prior to the conversion step (b) (i) of claim 1.

9. The method of claim 1, further comprising purifying/enriching the recovered isobutene.

10. The method of claim 1, wherein said microorganism is a bacterium, a yeast, a fungus or an algae.

11. A method for the production of isobutene from a carbon source characterized in that it comprise:

(a) culturing a microorganism capable of producing 3-methylcrotonic acid from a carbon source in a liquid culture medium, thereby producing said 3-methylcrotonic acid so that it accumulates in the liquid culture medium; and (b) converting said 3-methylcrotonic acid contained in the liquid culture medium obtained in step (a) into isobutene at a temperature between 180° C. and 400° C.; and (c) recovering the produced isobutene.

12. The method of claim 11, wherein the liquid culture medium containing said 3-methylcrotonic acid of step (a) is separated from the microorganism prior to step (b).

13. The method of claim 11, wherein said 3-methylcrotonic acid is isolated or purified from said liquid culture medium prior to step (b).

14. The method of claim 11, wherein said carbon source is metabolized into acetyl-CoA prior to its enzymatic conversion into 3-methylcrotonic acid.

15. The method of claim 14, wherein said carbon source is selected from the group consisting of glucose, fructose, sucrose, xylose, glycerol, starch, ethanol, lactic acid, acetic acid and a mixture thereof.

16. The method of claim 11, wherein said microorganism is pre-cultured in a suitable liquid culture medium under suitable conditions prior to the conversion step (b).

17. The method of claim 11, further comprising purifying/enriching the recovered isobutene.

18. The method of claim 11, wherein said microorganism is a bacterium, a yeast, a fungus or an algae.

* * * * *